United States Patent
Ye et al.

(10) Patent No.: US 12,046,056 B2
(45) Date of Patent: Jul. 23, 2024

(54) IMAGE ANNOTATION METHOD AND APPARATUS, ANNOTATION PRESENTATION METHOD AND APPARATUS, DEVICE, AND STORAGE MEDIUM

(71) Applicant: Tencent Technology (Shenzhen) Company Limited, Shenzhen (CN)

(72) Inventors: Hu Ye, Shenzhen (CN); Xiao Han, Shenzhen (CN); Kaiwen Xiao, Shenzhen (CN); Niyun Zhou, Shenzhen (CN); Mingyang Chen, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 418 days.

(21) Appl. No.: 17/379,839

(22) Filed: Jul. 19, 2021

(65) Prior Publication Data

US 2021/0350169 A1 Nov. 11, 2021

Related U.S. Application Data

(63) Continuation of application No. PCT/CN2020/089970, filed on May 13, 2020.

(30) Foreign Application Priority Data

May 29, 2019 (CN) .......................... 201910458139.3

(51) Int. Cl.
*G16H 30/40* (2018.01)
*G06F 16/51* (2019.01)
(Continued)

(52) U.S. Cl.
CPC ............ *G06V 20/698* (2022.01); *G06T 3/147* (2024.01); *G06T 7/0012* (2013.01); *G06V 10/945* (2022.01); *G16H 30/40* (2018.01)

(58) Field of Classification Search
CPC .... G06V 20/698; G06V 10/945; G16H 30/40; G06T 3/0075; G06T 7/0012
See application file for complete search history.

(56) References Cited

U.S. PATENT DOCUMENTS

| | | | |
|---|---|---|---|
| 8,305,457 B2 * | 11/2012 | Tsurumi | H04N 5/775 348/222.1 |
| 2010/0046842 A1 * | 2/2010 | Conwell | G06F 18/24 382/218 |

(Continued)

FOREIGN PATENT DOCUMENTS

| | | |
|---|---|---|
| CN | 101584210 A | 11/2009 |
| CN | 101719270 A | 6/2010 |

(Continued)

OTHER PUBLICATIONS

Tencent Technology, WO, PCT/CN2020/089970, Aug. 13, 2020, 5 pgs.

(Continued)

*Primary Examiner* — Shefali D Goradia
*Assistant Examiner* — D J Dhooge
(74) *Attorney, Agent, or Firm* — Morgan, Lewis & Bockius LLP

(57) ABSTRACT

A computer device obtains a to-be-annotated image having a first magnification. The device obtains an annotated image from an annotated image set, the annotated image distinct from the to-be-annotated image and having a second magnification that is distinct from with the first magnification. The annotated image set includes at least one annotated image. The device matches the to-be-annotated image with the annotated image to obtain an affine transformation matrix, and generates annotation information of the to-be-annotated image according to the affine transformation matrix and the annotated image. In this way, annotations corresponding to images at different magnifications may be (Continued)

migrated. For example, the annotations may be migrated from the low-magnification images to the high-magnification images, thereby reducing the manual annotation amount and avoiding repeated annotations, and further improving annotation efficiency and reducing labor costs.

19 Claims, 10 Drawing Sheets

(51) Int. Cl.
    *G06T 3/147* (2024.01)
    *G06T 7/00* (2017.01)
    *G06V 10/94* (2022.01)
    *G06V 20/69* (2022.01)
    *G16H 30/20* (2018.01)
    *G16H 50/70* (2018.01)

(56) References Cited

U.S. PATENT DOCUMENTS

2012/0283574 A1* 11/2012 Park .................. G06F 18/253
    600/476

2016/0307331 A1* 10/2016 Mollus ................ G16H 30/40
2017/0178307 A1* 6/2017 Yan ..................... G06T 5/50
2017/0310901 A1* 10/2017 Sheikh .................. G06T 3/18

FOREIGN PATENT DOCUMENTS

| | | |
|---|---|---|
| CN | 102360513 A | 2/2012 |
| CN | 102737379 A | 10/2012 |
| CN | 103390282 A | 11/2013 |
| CN | 104586418 A | 5/2015 |
| CN | 105260733 A | 1/2016 |
| CN | 105488754 A | 4/2016 |
| CN | 108573279 A | 9/2018 |
| CN | 109584250 A | 4/2019 |
| CN | 109754387 A | 5/2019 |
| CN | 110175255 A | 8/2019 |
| JP | 2003046857 A | 2/2003 |

OTHER PUBLICATIONS

Tencent Technology, IPRP, PCT/CN2020/089970, Nov. 16, 2021, 6 pgs.
Tencent Technology, Isr, PCT/CN2020/089970, Aug. 13, 2020, 2 pgs.

* cited by examiner

IMAGE ANNOTATION METHOD AND APPARATUS, ANNOTATION PRESENTATION METHOD AND APPARATUS, DEVICE, AND STORAGE MEDIUM

RELATED APPLICATION

This application is a continuation application of PCT Patent Application No. PCT/CN2020/089970, entitled "IMAGE LABELING METHOD, LABELING DISPLAY METHOD, APPARATUS, DEVICE, AND STORAGE MEDIUM" filed on May 13, 2020, which claims priority to Chinese Patent Application No. 201910458139.3, filed with the State Intellectual Property Office of the People's Republic of China on May 29, 2019, and entitled "IMAGE LABELING METHOD, LABELING DISPLAY METHOD, APPARATUS, DEVICE, AND STORAGE MEDIUM", all of which are incorporated herein by reference in their entirety.

FIELD OF THE TECHNOLOGY

This application relates to the field of artificial intelligence (AI), and in particular, to an image annotation method and apparatus, an annotation presentation method and apparatus based on a pathological image, a device, and a computer storage medium.

BACKGROUND OF THE DISCLOSURE

With the development of artificial intelligence (AI) technologies such as machine learning (ML) and deep learning (DL), medical treatment has become an important research and application field in the AI industry. Intelligent medical treatment involves a plurality of important fields in medical imaging, pathological diagnosis, new drug research and development, intelligent assistance, and the like. The pathological diagnosis is an important standard for disease diagnosis, and pathological section analysis provides a reliable basis for the pathological diagnosis.

In the related art, pathological images are generally annotated in a manual annotation manner. That is, a to-be-annotated pathological image is generally annotated manually, and the annotation result is then checked. If an abnormal annotation is found, the image is returned for modification until annotation of all pathological images is completed.

However, because experiential knowledge needs to be considered during manual annotation, and an annotator may miss annotating images or make mistakes during annotation due to factors such as fatigue, a professional doctor further needs to examine annotated pathological images, resulting in a high annotation workload and high labor costs.

SUMMARY

Embodiments of this application provide an image annotation method and apparatus, an annotation presentation method and apparatus based on a pathological image, a device, and a computer storage medium, to migrate annotations corresponding to images at different magnifications. For example, annotations on low-magnification images may be migrated to high-magnification images, thereby reducing the manual annotation amount and avoiding repeated annotations, and further improving annotation efficiency and reducing labor costs.

In view of this, an embodiment of this application provides an image annotation method, including:
obtaining a to-be-annotated image corresponding to a first magnification;
obtaining an annotated image from an annotated image set, the annotated image distinct from the to-be-annotated image and having a second magnification that is distinct from the first magnification, the annotated image set including at least one annotated image;
matching the to-be-annotated image with the annotated image to obtain (e.g., determine) an affine transformation matrix; and
generating annotation information of the to-be-annotated image according to the affine transformation matrix and the annotated image.

An embodiment of this application further provides an annotation presentation method based on a pathological image, the method including:
obtaining a to-be-annotated pathological image corresponding to a first magnification;
obtaining an annotated pathological image from an annotated pathological image set, the annotated pathological image corresponding to a second magnification, the second magnification distinct from the first magnification, the annotated pathological image set including at least one annotated pathological image;
matching the to-be-annotated pathological image with the annotated pathological image to obtain (e.g., determine) an affine transformation matrix;
generating pathological annotation information of the to-be-annotated pathological image according to the affine transformation matrix and the annotated pathological image; and
presenting the pathological annotation information of the to-be-annotated pathological image.

An embodiment of this application further provides an image annotation apparatus (e.g., a computer device, an electronic device, a computer system, etc.), including:
an obtaining module, configured to obtain a to-be-annotated image, the to-be-annotated image corresponding to a first magnification,
the obtaining module further configured to obtain an annotated image from an annotated image set, the annotated image corresponding to a second magnification, the second magnification distinct from the first magnification, the annotated image set including at least one annotated image;
a matching module, configured to match the to-be-annotated image with the annotated image obtained by the obtaining module to obtain (e.g., determine) an affine transformation matrix; and
an annotation module, configured to generate annotation information of the to-be-annotated image according to the affine transformation matrix obtained through matching by the matching module and the annotated image.

An embodiment of this application further provides an annotation presentation apparatus, including:
an obtaining module, configured to obtain a to-be-annotated pathological image, the to-be-annotated image corresponding to a first magnification,
the obtaining module further configured to obtain an annotated pathological image from an annotated pathological image set, the annotated pathological image corresponding to a second magnification, the second magnification being inconsistent with (e.g., distinct from) the first magnification, the annotated pathological image set including at least one annotated pathological image;

a matching module, configured to match the to-be-annotated pathological image with the annotated pathological image obtained by the obtaining module to obtain (e.g., determine) an affine transformation matrix;

an annotation module, configured to generate pathological annotation information of the to-be-annotated pathological image according to the affine transformation matrix obtained through matching by the matching module and the annotated pathological image; and a presentation module, configured to present the pathological annotation information of the to-be-annotated pathological image obtained through annotation by the annotation module.

An embodiment of this application further provides a terminal device (e.g., a computer device, an electronic device, etc.), including a memory and a processor, the memory configured to store a computer program; and
the processor configured to perform the image annotation method according to the embodiments of this application when executing the computer program in the memory.

An embodiment of this application further provides a terminal device (e.g., a computer device, an electronic device, etc.), including a memory and a processor, the memory configured to store a computer program; and
the processor configured to perform the annotation presentation method based on a pathological image according to the embodiments of this application when running the computer program in the memory.

An embodiment of this application further provides a non-transitory computer readable storage medium, storing computer executable instructions, the computer executable instructions configured to perform the image annotation method according to the embodiments of this application.

An embodiment of this application further provides a non-transitory computer readable storage medium, storing computer executable instructions, the computer executable instructions configured to perform the annotation presentation method based on a pathological image according to the embodiments of this application.

The application of the image annotation method and apparatus, the annotation presentation method and apparatus based on a pathological image, the device, and the non-transitory computer readable storage medium according to the embodiments of this application has at least the following beneficial technical effects:

matching the to-be-annotated image with the annotated image to obtain an affine transformation matrix, and generating annotation information of the to-be-annotated image according to the affine transformation matrix and the annotated image. Because the magnification of the to-be-annotated image is different from the magnification of the annotated image, annotations corresponding to images at different magnifications may be migrated. For example, annotations may be migrated from low-magnification images to high-magnification images, thereby reducing the manual annotation amount and avoiding repeated annotations, and further improving annotation efficiency and reducing labor costs.

DESCRIPTION OF EMBODIMENTS

Figure 1:
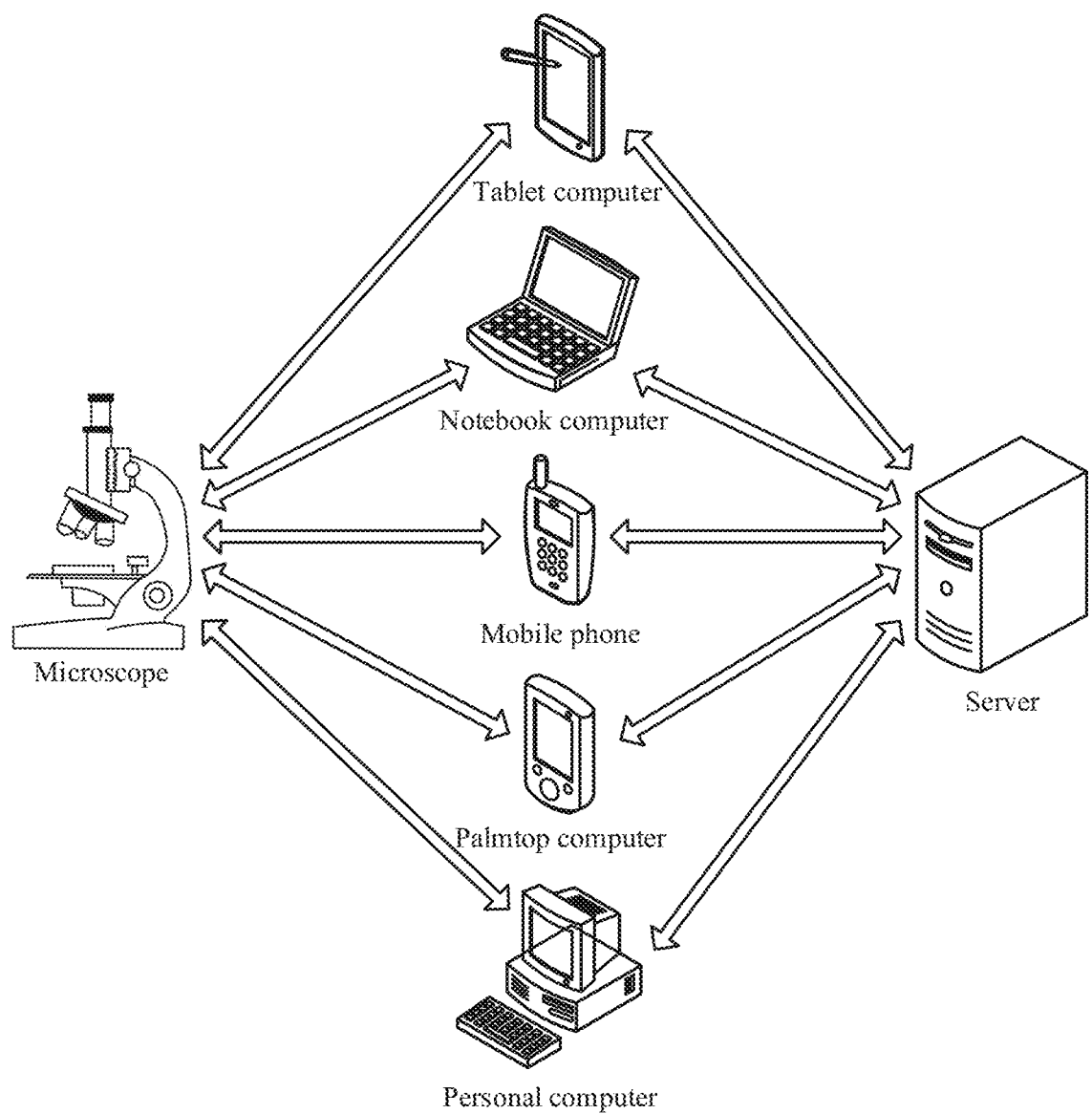
FIG. 1 is a schematic architectural diagram of an image annotation system according to an embodiment of this application.

Embodiments of this application provide an image annotation method and apparatus, and an annotation presentation method and apparatus based on a pathological image, to migrate annotations corresponding to images at different magnifications, for example, to migrate annotations of low-magnification images to high-magnification images, thereby reducing an amount of manual annotation and avoiding repeated annotations, and further improving annotation efficiency and reducing labor costs.

In the specification, claims, and accompanying drawings of this application, the terms "first", "second", "third", "fourth", and the like (if existing) are intended to distinguish between similar objects rather than describe a specific sequence or a precedence order. Data used in this way may be interchanged in an appropriate case, so that the embodiments of this application described herein can be implemented in a sequence other than the sequence illustrated or described herein. In addition, the terms "include", "corresponding to" and any other variants are intended to cover the non-exclusive inclusion. For example, a process, method, system, product, or device that includes a series of steps or units is not necessarily limited to those expressly listed steps or units, but may include other steps or units not expressly listed or inherent to such a process, method, product, or device.

The image annotation method and the annotation presentation method based on a pathological image provided in the embodiments of this application are applicable to the field of artificial intelligence (AI), for example, to a medical field (a scenario of annotating a pathological image), a speech recognition field (a scenario of annotating speech information, for example, audio A and audio B have the same audio segment), or a monitoring field (a scenario of annotating images such as different people and vehicles). During image preprocessing, it is assumed that there are numerous images (e.g., 50,000 images, 100,000 images, 300,000 images etc.) that need to be annotated, where a subset of the images (e.g., 1000 images, 5000 images etc.) are annotated in a manual annotation manner, and the remaining images are all images at different magnifications corresponding to the annotated images. Therefore, an affine transformation matrix between images with a correspondence is separately calculated (e.g., determined), and annotation information of an annotated image is migrated to an unannotated image according to the affine transformation matrix. In this way, it is unnecessary to annotate all the images.

With the fast development of science and technologies, AI is also increasingly widely applied in the medical industry. The most common medical images in the medical field include, but not limited to, a blood vessel pathological image, a cardiovascular image, a computerized tomography (CT) image, a B-mode ultrasound image, and a pathological image. The pathological image is a magnified image of a tissue section of a patient's pathological part under a microscope. Because the pathological image directly reflects a lesion inside the tissue, and is an important basis for disease diagnosis of a doctor and even a final diagnosis basis for some diseases. For example, in cancer diagnosis, a doctor observes a radiographic image of a lesion, including observing whether there is a shadow, a plaque or vessel dilatation.

With the increasing patients and higher requirements for diagnostic accuracy of diseases, the quantity of pathological examinations, especially analyses of microscopic images, has grown exponentially, which increases the workload of pathology laboratory experts and requires more personnel. A pathological section generally includes millions of cells. This brings a heavy workload to doctors, and the doctors may read images with fatigue. In addition, pathological diagnosis of a doctor generally is highly subjective, and a pathologist with less experience may have a misdiagnosis. These factors make it particularly important to develop AI-based pathological diagnosis, and intelligent analysis of the pathological section can improve the diagnostic accuracy and working efficiency of a physician. However, AI technology such as machine learning (ML) and deep learning requires training data sets with a huge data amount. This becomes the key factor restricting the wide application of the AI technology in pathological diagnosis and analysis. To annotate data of a large quantity of pathological microscope images generally consumes tremendous labor and material resources. In addition, the pathological diagnosis generally needs to be performed at different magnifications, and image data at different magnifications need to be annotated. As a result, the workload is undoubtedly increased.

An embodiment of this application provides an image annotation method, in which image annotations at different magnifications may be quickly obtained by annotating only low-magnification images, thereby accelerating the image annotation speed and promoting the application of the AI technology in pathological diagnosis. The image annotation method provided in this embodiment of this application is applicable to an image annotation system shown in FIG. 1. FIG. 1 is a schematic architectural diagram of an image annotation system according to an embodiment of this application. As shown in FIG. 1, the image annotation system may include an image acquisition device and a terminal device. The image acquisition device may be a microscope or another imaging device, configured to send acquired images to the terminal device, and a doctor annotates some images on the terminal device. The terminal device migrates annotation information of the annotated images to unannotated images.

In some embodiments, the image annotation system may include a terminal device and a server. The server stores a large quantity of images, and the doctor obtains some images from the server by using the terminal device for annotation. The terminal device sends the annotated images to the server. The server migrates annotation information of the annotated images to unannotated images.

In some embodiments, the image annotation system may include an image acquisition device, a terminal device, and a server. The image acquisition device may be a microscope or another imaging device, configured to send acquired images to the terminal device, and a doctor annotates some images on the terminal device. The terminal device sends the annotated images to the server. The server migrates annotation information of the annotated images to unannotated images.

An embodiment of this application further provides an image annotation apparatus for implementing the image annotation method. The image annotation apparatus is applicable to a terminal device (e.g., computer device, electronic device, etc.) or a computer server system.

The terminal device includes, but not limited to, a tablet computer, a notebook computer, a palmtop computer, a mobile phone, a speech interaction device, and a personal computer (PC), which is not limited herein.

Figure 2:
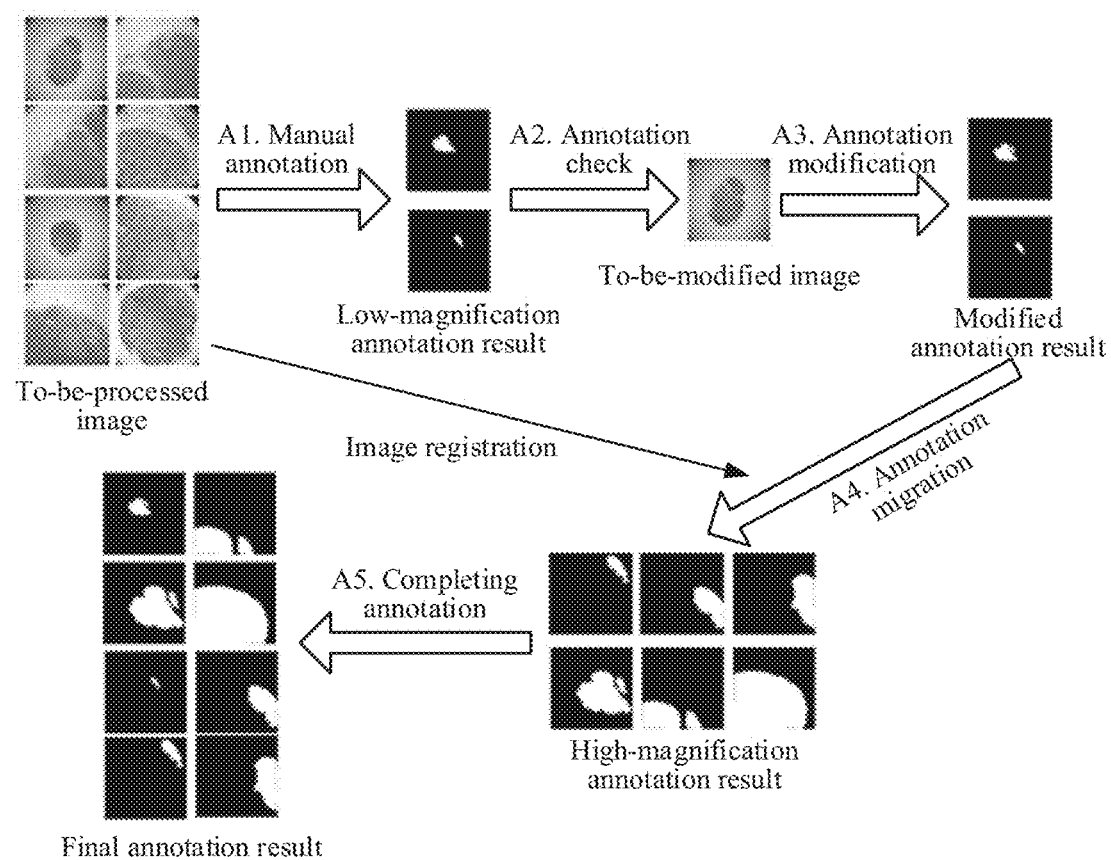
FIG. 2 is a schematic flowchart of performing annotation based on a pathological image according to an embodiment of this application.

Referring to FIG. 2, FIG. 2 is a schematic flowchart of performing annotation based on a pathological image according to an embodiment of this application. As shown in the figure, in step A1, to-be-processed images are obtained, and low-magnification images corresponding to the to-be-processed images are manually annotated. In step A2, manually annotated low-magnification annotation results are checked. If an image with an annotation error is found, the image is used as a to-be-modified image. Then, in step A3, the to-be-modified image is annotated for modification, to obtain a modified annotation result. In step A4, high-magnification images corresponding to the to-be-processed images are registered with modified low-magnification images, and annotations are migrated from the low-magnification images to the high-magnification images based on registration results, to obtain high-magnification annotation results. In step A5, annotations of all the to-be-processed images are completed, to obtain final annotation results.

It can be learned that in the foregoing manner, the workload of the manual data annotation can be reduced, some repeated annotations during annotation modification, thereby improving the efficiency of annotating the pathological microscope images, and accelerating the development and application of the AI technology in pathological diagnosis. The image annotation method provided in this embodiment of this application is applicable to AI-based pathological diagnosis projects, such as breast cancer lymphatic metastasis prediction and mitosis detection, to more quickly and efficiently obtain annotated pathological image data, meet data requirements of the AI-based pathological diagnosis projects, and accelerate a project iteration speed.

Figure 3:
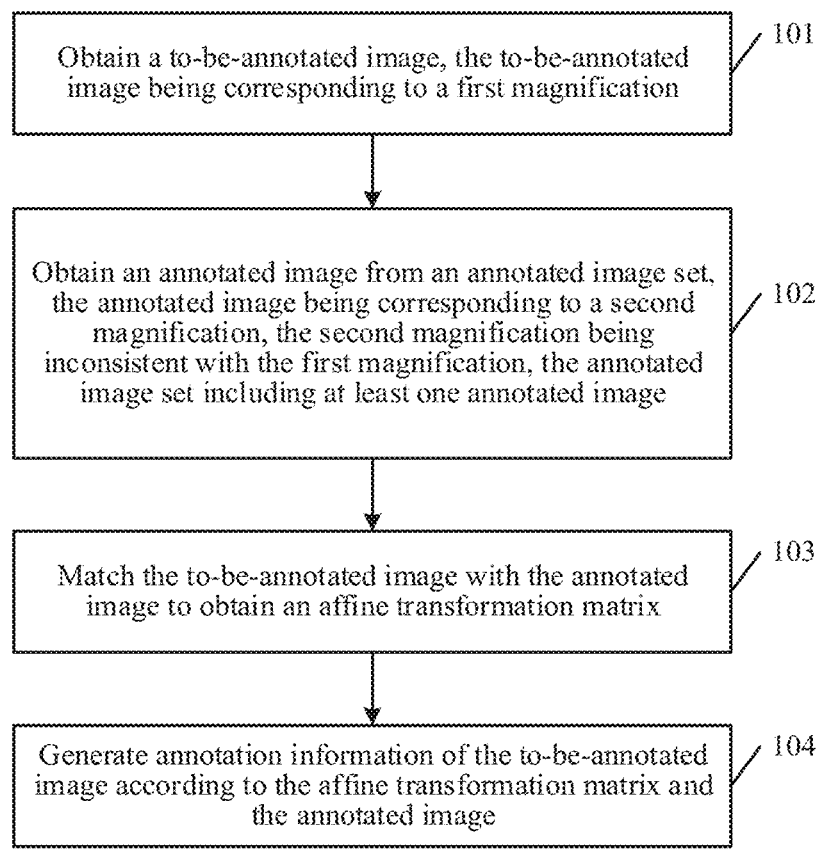
FIG. 3 is a schematic flowchart of an image annotation method according to an embodiment of this application.

The image annotation method provided in this embodiment of this application is described below with reference to the foregoing description. Referring to FIG. 3, the image annotation method provided in this embodiment of this application includes the following steps:

Step 101. Obtain a to-be-annotated image, the to-be-annotated image corresponding to a first magnification.

In this embodiment, the image annotation apparatus obtains the to-be-annotated image, the to-be-annotated image corresponding to the first magnification. In actual application, a magnification corresponding to an image may be set according to actual requirements. For example, the first magnification may be a relatively high magnification, such as a magnification of 100 times, or a magnification of 50 times, etc.

Step 102. Obtain an annotated image from an annotated image set, the annotated image corresponding to a second magnification, the second magnification is distinct from (e.g., inconsistent with) the first magnification, the annotated image set including at least one annotated image.

During actual implementation, the image annotation apparatus obtains the annotated image from the annotated image set. The annotated image set includes at least one annotated image, the annotated image corresponds to the second magnification, the second magnification is less than the first magnification, or the second magnification is greater than the first magnification. If only low-magnification images are annotated, and high-magnification images are then registered with the low-magnification images to obtain annotations on the high-magnification images, the first magnification is less than the second magnification. If only high-magnification images are annotated, and low-magnification images are then registered with the high-magnification images to obtain annotations on the low-magnification images, the first magnification is greater than the second magnification.

Step 103. Match the to-be-annotated image with the annotated image to obtain an affine transformation matrix.

During actual implementation, the image annotation apparatus matches the to-be-annotated image with the annotated image to obtain an affine transformation matrix through affine transformation.

The affine transformation herein is a linear transformation between two-dimensional coordinates, through which flatness (that is, a straight line is still a straight line after transformation and is not bent, and an arc is still an arc) and parallelism (that is, a relative position relationship between two-dimensional graphics is unchanged, parallel lines are still parallel lines, and an angle between intersecting straight lines is unchanged) of the two-dimensional graphics are maintained. The affine transformation may be implemented by using a combination of a series of atomic transformations, including translation, scale, flip, rotation, and shear. Therefore, the five changes are a process of transforming an original image into a transformed image, and may be described by using the affine transformation matrix.

After a matching point pair of the to-be-annotated image and the annotated image is obtained, the affine transformation matrix may be calculated, to implement transformation from the original image (the annotated image) to a new image (the to-be-annotated image). After the affine transformation matrix is obtained, the same transformation may be applied to an annotation of the original image (the annotated image), to obtain a migrated annotation on the new image (the to-be-annotated image).

Step 104. Generate annotation information of the to-be-annotated image according to the affine transformation matrix and the annotated image.

During actual implementation, the image annotation apparatus determines a position relationship between the to-be-annotated image and the annotated image according to the affine transformation matrix. It is assumed that the annotated image includes an annotation of a region A, and it can be determined according to the affine transformation matrix that the region A also appears in the to-be-annotated image. Therefore, the annotation of the region A is migrated to the to-be-annotated image.

Through the application of the foregoing embodiments in the present invention, annotations corresponding to images at different magnifications may be migrated. For example, the annotations may be migrated from the low-magnification images to the high-magnification images, thereby reducing the manual annotation amount and avoiding repeated annotations, and further improving annotation efficiency and reducing labor costs.

During actual implementation, image annotation may be performed by using a plurality of (e.g., at least two) annotated images, which is described below.

In some embodiments, the annotated image may be obtained from the annotated image set in the following manner: obtaining a first annotated image and a second annotated image from the annotated image set.

Correspondingly, the matching the to-be-annotated image with the annotated image to obtain an affine transformation matrix includes: matching the to-be-annotated image with the first annotated image to obtain a first affine transformation matrix, and matching the to-be-annotated image with the second annotated image to obtain a second affine transformation matrix.

Correspondingly, the generating annotation information of the to-be-annotated image according to the affine transformation matrix and the annotated image includes:

generating first annotation information of the to-be-annotated image according to the first affine transformation matrix and the first annotated image;

generating second annotation information of the to-be-annotated image according to the second affine transformation matrix and the second annotated image; and generating the annotation information of the to-be-annotated image according to the first annotation information and the second annotation information.

Figure 4:
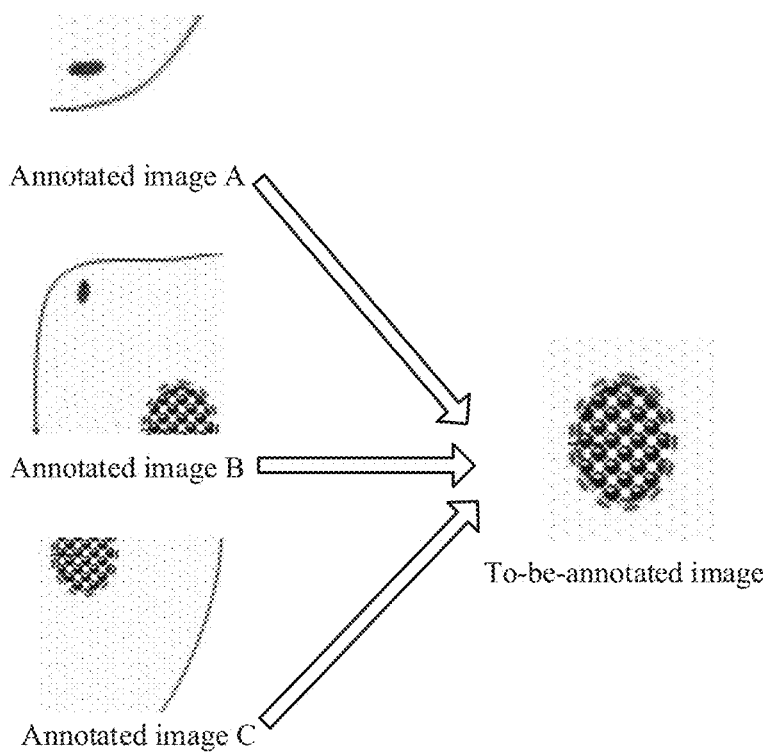
FIG. 4 is a schematic diagram of matching with a plurality of images one by one according to an embodiment of this application.

Description is made by using an example in which image annotation is performed by using a plurality of annotated images. FIG. 4 is a schematic diagram of matching with a plurality of images one by one according to an embodiment of this application. Referring to FIG. 4, it is assumed that an annotated image set includes 3 annotated images: an annotated image A, an annotated image B, and an annotated image C. The annotated image A is matched with the to-be-annotated image, but the matching fails. Therefore, the annotated image B is matched with the to-be-annotated image; it is determined that a matching relationship exists between the annotated image B and the to-be-annotated image through affine transformation; a first affine transformation matrix is obtained, and first annotation information of the to-be-annotated image may be determined according to the first affine transformation matrix. Then, the annotated image C is matched with the to-be-annotated image; it is determined that a matching relationship exists between the annotated image C and the to-be-annotated image through affine transformation; a second affine transformation matrix is obtained, and second annotation information of the to-be-annotated image may be determined according to the second affine transformation matrix. Finally, a union set between the first annotation information and the second annotation information is obtained. That is, a plurality of matching results are combined to obtain annotation information of the to-be-annotated image.

Figure 6:
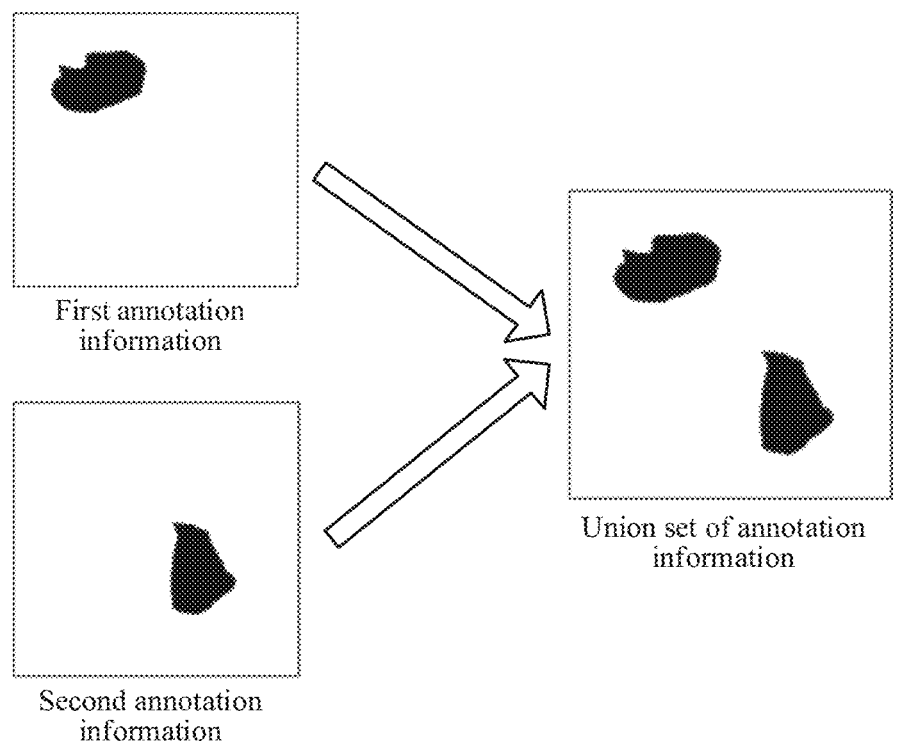
FIG. 6 is a schematic diagram of combining a plurality of matching results according to an embodiment of this application.

The combination of the plurality of matching results is described herein. FIG. 6 is a schematic diagram of combining a plurality of matching results according to an embodiment of this application. Referring to FIG. 6, during actual acquisition of images, a portion of a high-magnification image may appear in a low-magnification image, while another portion of the high-magnification image appears in another low-magnification image. In this case, it is necessary to separately match the high-magnification image with a plurality of low-magnification images, to obtain a complete annotation result. That is, first annotation information obtained by matching the high-magnification image with a first low-magnification image is combined with second annotation information obtained by matching the high-magnification image with a second low-magnification image, to obtain a union set of annotation information as annotation information of the high-magnification image. On the contrary, if a portion of a low-magnification image appears in a high-magnification image, while another portion of the low-magnification image appears in another high-magnification image, it is necessary to separately match the low-magnification image with a plurality of high-magnification images, to obtain a complete annotation result. That is, first annotation information obtained by matching the low-magnification image with a first high-magnification image is combined with second annotation information obtained by matching the low-magnification image with a second high-magnification image, to obtain a union set of annotation information as annotation information of the low-magnification image.

When one high-magnification image is matched with a plurality of low-magnification images, if the one-by-one matching method is used, a union set of all matching results may be obtained. Considering that a low-magnification image has a wider field of view, for the same size of the field of view, a plurality of high-magnification images need to be acquired for matching.

Through the application of the foregoing embodiments of this application, different annotated images are separately matched with the to-be-annotated image, to obtain different affine transformation matrices, and further obtain different annotation information based on the different affine transformation matrices; a union operation is performed on all the obtained annotation information, to obtain annotation information of the to-be-annotated image. In this way, the to-be-annotated image is annotated by using a plurality of annotated images, thereby effectively improving the annotation accuracy and enhancing the annotation adaptability.

Image annotation performed by using a plurality of annotated images is still used as an example for description.

In some embodiments, the annotated image may be obtained from the annotated image set in the following manner: obtaining a plurality of annotated images from the annotated image set, the plurality of annotated images having overlapping parts;

Correspondingly, the matching the to-be-annotated image with the annotated image to obtain an affine transformation matrix includes: splicing the plurality of annotated images to obtain a to-be-matched image; and matching the to-be-annotated image with the to-be-matched image to obtain the affine transformation matrix.

Correspondingly, the generating annotation information of the to-be-annotated image according to the affine transformation matrix and the annotated image includes: generating the annotation information of the to-be-annotated image according to the affine transformation matrix and the to-be-matched image.

Figure 5:
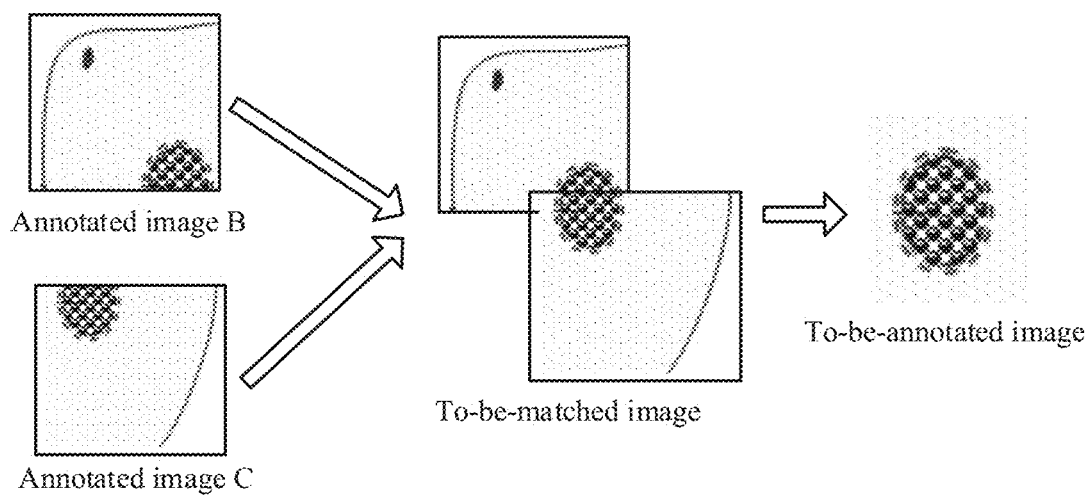
FIG. 5 is a schematic diagram of splicing and matching with a plurality of images according to an embodiment of this application.

For example, FIG. 5 is a schematic diagram of splicing and matching with a plurality of images according to an embodiment of this application. Referring to FIG. 5, it is assumed that an annotated image set includes an annotated image B and an annotated image C, and the annotated image B and the annotated image C have overlapping parts. The two annotated images are spliced to obtain a to-be-matched image, and the to-be-matched image is then matched with the to-be-annotated image. A matching relationship between the to-be-matched image and the to-be-annotated image is determined through affine transformation, an affine transformation matrix is obtained, and annotation information of the to-be-annotated image may be determined according to the affine transformation matrix.

It may be understood that when there are three or more annotated images, the images may be spliced provided that the images have overlapping parts, to obtain a to-be-matched image.

The image splicing in this embodiment of this application refers to splicing a plurality of images having overlapping parts into a large image according to a position association, and the splicing requires acquired images to have overlapping parts. In this way, the images may be matched and thus the splicing are completed. The image splicing refers to splicing a plurality of images photographed at different times, from different views, or by different sensors into a coherent image. Due to a complex motion state of a camera, planar images photographed by the camera also have various differences, and there is usually a complex transformation relationship between two to-be-matched images. Due to different representation dimensions, different images need to be transformed into the same representation dimension by using a specific transformation model, to implement splicing.

In some embodiments, before the obtaining an annotated image from an annotated image set, the method may further include:

obtaining a target annotation region; obtaining a plurality of to-be-processed images according to the target annotation region, the plurality of to-be-processed images including the to-be-annotated image and M annotatable images, M is an integer greater than or equal to 1; receiving annotation information corresponding to each annotatable image in the M annotatable images; and generating the annotated image set according to the annotation information corresponding to the each annotatable image, the annotated image set including M annotated images. In this way, the images are pre-annotated, and during manual annotation, only some images rather than all images in the to-be-processed images need to be annotated, thereby reducing annotation costs and improving annotation efficiency.

In actual application, first, a target annotation region, for example, a cell of a certain tissue of a lung is determined. Annotated images for the cell of the tissue may be classified into a small group, so that annotation efficiency can be improved according to annotation types. Next, a plurality of to-be-processed images are photographed by a microscope or another imaging device, where the plurality of to-be-processed images include images at different magnifications. It is assumed that there are 20 to-be-processed images, where a magnification of 4 to-be-processed images is 40 times, and a magnification of remaining 16 to-be-processed images is 400 times. That is, the plurality of to-be-processed images include 16 to-be-annotated images and 4 (M=4) annotatable images. A doctor may manually annotate the M annotatable images, that is, annotate a small quantity of images. The image annotation apparatus receives annotation information corresponding to each annotatable image in the M annotatable images. Finally, an annotated image set is generated with reference to the annotation information corresponding to the each annotatable image. That is, the annotated image set includes M annotated images. The annotation information on the annotated images may be migrated to the remaining to-be-annotated images through an affine transformation matrix.

It may be understood that, if it is found that the annotation is inaccurate after manual check, the image may be returned to modify the annotation, to finally obtain an accurate annotation result.

During this process, manual annotation includes, but not limited to, point annotation, line annotation, and region annotation, where the region annotation includes, but not limited to, annotation forms of a polygon and a free curve.

In some embodiments, annotation information corresponding to each annotatable image in the M annotatable images may be received in the following manner:
receiving an image annotation instruction, the image annotation instruction carrying an identifier of an annotatable image; and annotating the annotatable image according to the image annotation instruction to obtain annotation information corresponding to the annotatable image. In this case, image annotation is implemented, and feasibility and operability are achieved.

By using the method of manually annotating the images provided in this embodiment of this application, a user may annotate each annotatable image by using the terminal device. In actual application, the user may choose to annotate the images in batches or annotate the images one by one. It is assumed that M is 100, that is, there are 100 annotatable images. 10 annotatable images may be displayed on the terminal device at a time, and the user annotates the 10 annotatable images in a manner of clicking a region and entering text. That is, an image annotation instruction is triggered. Each image annotation instruction corresponds to an identifier of one annotatable image, so that the image annotation apparatus determines annotation information of the annotatable image. When annotation of annotatable images on a page is completed, annotatable images on a next page may be annotated.

Similarly, only one annotatable image may be displayed on the terminal device at a time, and the user annotates the annotatable image in a manner of clicking a region and entering text. That is, an image annotation instruction is triggered. Each image annotation instruction corresponds to an identifier of one annotatable image, so that the image annotation apparatus determines annotation information of the annotatable image. When annotation of the annotatable image is completed, a next annotatable image may be annotated.

In some embodiments, the to-be-annotated image is matched with the annotated image to obtain an affine transformation matrix in the following manner:
obtaining a first feature point set of the to-be-annotated image, the first feature point set including a plurality of feature points; obtaining a second feature point set of the annotated image, the second feature point set including a plurality of feature points; matching the first feature point set with the second feature point set to obtain a matching result; and obtaining the affine transformation matrix through calculation according to the matching result. In this way, a similarity between the two images is determined by matching the feature points, and the affine transformation matrix is generated based on a matching relationship between the feature points. Considering that an image includes many feature points, a richer amount of information is obtained, so that higher matching accuracy is achieved.

In actual application, a first feature point set is obtained from a to-be-annotated image, where the first feature point set includes a plurality of feature points, and it is assumed that there are 200 feature points. Similarly, a second feature point set is obtained from an annotated image, where the second feature point set includes a plurality of feature points, and it is assumed that there are 190 feature points. Therefore, each feature point in the first feature point set is matched with the feature points in the second feature point set. Assuming that a point A in the first feature point set is successfully matched with a point B in the second feature point set, a matching result indicating that the point A and the point B are matching points is obtained, and an affine transformation matrix is determined based on all matching points that are successfully matched. The affine transformation matrix may be expressed as:

$$\begin{bmatrix} x' \\ y' \\ 1 \end{bmatrix} = \begin{bmatrix} m00 & m01 & m02 \\ m10 & m11 & m12 \\ 0 & 0 & 1 \end{bmatrix} \begin{bmatrix} x \\ y \\ 1 \end{bmatrix} = \begin{bmatrix} m00^*x + m01^*y + m02 \\ m10^*x + m11^*y + m12 \\ 1 \end{bmatrix}$$

where the affine transformation matrix transforms original coordinates (x, y) into new coordinates (x', y'), the original coordinates may come from the feature points of the second feature point set, and the new coordinates may come from the feature points of the first feature point set.

It may be understood that feature point types used in this application include, but not limited to, scale invariant feature transform (SIFT), speeded up robust features (Surf), and histogram of oriented gradient (HOG). SIFT feature points are described below.

SIFT is to detect and describe local features in images, find extreme points in a spatial scale, and extract position, scale and rotation invariants. A SIFT feature is a local feature of an image, remains invariant to rotation, scaling, and a brightness change, and thus may be used as a feature point for image registration. A SIFT algorithm is implemented in various open-source libraries such as OpenCV, and the algorithm mainly includes the following process:
(a) establishing a scale space, and detecting extreme points in the scale space;
(b) accurately positioning feature points, and removing unstable feature points;
(c) specifying a main direction parameter for each feature point; and
(d) collecting statistics on feature point neighborhood information to generate feature descriptors, that is, the feature points.

In actual application, first, extreme value detection in the scale space is performed. That is, all images in the scale space are searched, and potential points of interest invariant to a scale and selection are recognized by using a Gaussian differential function. Then, the feature points are positioned. That is, at each candidate position, a position scale is determined by using a fitting fine model, and key points are selected according to a degree of stability. Next, feature direction assignment is performed. That is, one or more directions are assigned to each key point position based on a local gradient direction of an image, and all subsequent operations are transformation for the direction, the scale and the position of the key point to provide invariance of the features. Finally, the feature points are described. That is, local gradients of an image are measured at a designated scale in a neighborhood around each feature point. The gradients are transformed into a representation, and the representation allows a relatively large local shape deformation and illumination change.

In some embodiments, the first feature point set may be matched with the second feature point set to obtain a matching result in the following manner:

determining a to-be-matched feature point from the second feature point set;

determining a first feature point and a second feature point from the first feature point set according to the to-be-matched feature point;

determining a first distance according to the first feature point and the to-be-matched feature point, and determining a second distance according to the second feature point and the to-be-matched feature point, the first distance is less than the second distance; and determining, when a ratio of the first distance to the second distance is less than a ratio threshold, that the first feature point is successfully matched with the to-be-matched feature point.

Figure 7:
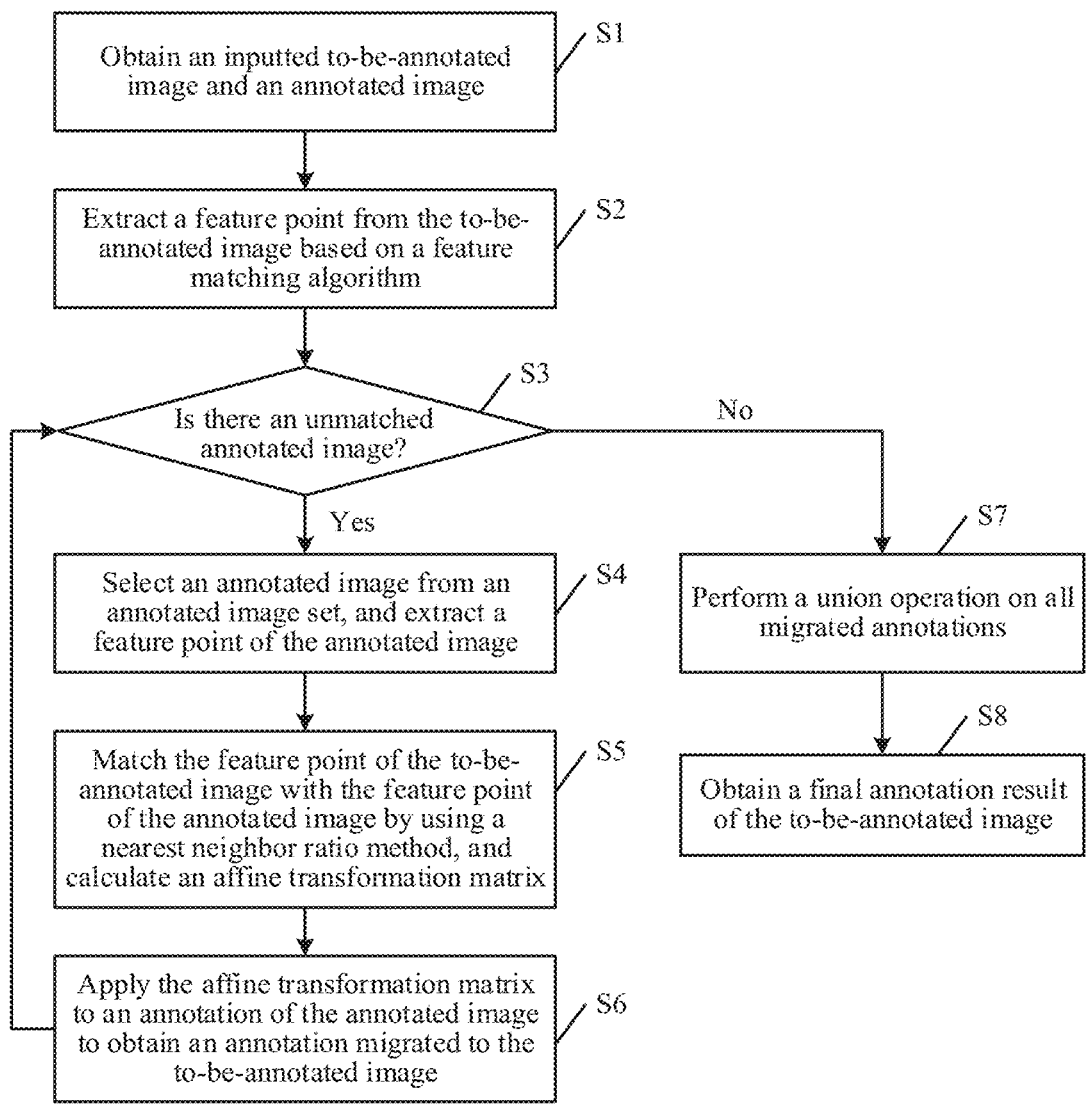
FIG. 7 is a schematic flowchart of a method of matching feature points according to an embodiment of this application.

The matching of the feature points is described in FIG. 7, which shows a schematic flowchart of a method of matching feature points according to an embodiment of this application. Referring to FIG. 7, the method of matching feature points provided in this embodiment of this application includes the following steps:

Step S1. Obtain an inputted to-be-annotated image and an annotated image.

During actual implementation, the image annotation apparatus may first obtain the inputted to-be-annotated image and the annotated image (e.g., a first image to be annotated, and a second image that has been annotated). It is assumed that the to-be-annotated image (e.g., first image) is a high-magnification image, and in this case, the annotated image (e.g., second image) may be a low-magnification image that needs to be registered. It may be understood that there may be a plurality of low-magnification images that need to be registered.

Step S2. Extract a feature point from the to-be-annotated image based on a feature matching algorithm.

During actual implementation, a feature point of the high-magnification image may be calculated based on the SIFT algorithm.

Step S3. Determine whether there is an unmatched annotated image; if yes, perform step S4; if not, perform step S7.

Herein, the determining whether there is an unmatched annotated image may be: determining whether there is an unmatched low-magnification image.

Step S4. Select an annotated image from an annotated image set, and extract a feature point of the annotated image.

For example, a low-magnification image is first selected, and a feature point is extracted from the low-magnification image based on the SIFT algorithm.

Step S5. Match the feature point of the to-be-annotated image with the feature point of the annotated image by using a nearest neighbor ratio method, and calculate an affine transformation matrix.

During actual implementation, assuming that the to-be-annotated image is a high-magnification image, and the annotated image is a low-magnification image, a to-be-matched feature point is determined from a second feature point set corresponding to the low-magnification image, a first feature point and a second feature point are then determined from a first feature point set corresponding to the high-magnification image according to the to-be-matched feature point, a first distance is then determined according to the first feature point and the to-be-matched feature point, and a second distance is determined according to the second feature point and the to-be-matched feature point. If a ratio of the first distance to the second distance is less than a ratio threshold, it is determined that the first feature point is successfully matched with the to-be-matched feature point. An affine transformation matrix may be obtained through calculation in the foregoing manner.

Step S6. Apply the affine transformation matrix to an annotation of the annotated image to obtain an annotation migrated to the to-be-annotated image.

For example, an annotation of the low-magnification image is migrated to the high-magnification image, to obtain annotation information of the high-magnification image.

Step S7. Perform a union operation on all migrated annotations.

Herein, step S3 to step S6 are repeated until registration and annotation migration of the to-be-annotated images and all the annotated images are completed, for example, registration and annotation migration of the high-magnification images and all the low-magnification images are completed. If there has been no low-magnification image, a union operation is performed on all the migrated annotations.

Step S8. Obtain a final annotation result of the to-be-annotated image.

The nearest neighbor ratio method is described below. For a to-be-matched feature point p of an annotated image during matching of feature points, first two feature points nearest to the to-be-matched feature point p, that is, a first feature point q1 and a second feature point q2, are searched for in a to-be-matched image, where a distance between adjacent descriptors of the to-be-matched feature point p and the first feature point q1 is D1, and a distance between adjacent descriptors of the to-be-matched feature point p and the second feature point q2 is D2, where D1 is less than D2. If a ratio obtained by dividing the shortest distance D1 by the second shortest distance D2 is less than a ratio threshold T, it is considered that the first feature point q1 having the shortest distance is more likely to be a true matching point, thereby determining that the first feature point is successfully matched with the to-be-matched feature point. A matching formula of the nearest neighbor ratio method is as follows:

$$\frac{D1}{D2} < T.$$

Through the application of the method of matching the feature points provided in this embodiment of this application, during matching of the feature points, a nearest neighbor of a query point may be found based on a similarity measurement criterion and a search policy, but two points having the shortest distance are not necessarily a correct matching point pair. To reduce errors during subsequent processing, based on initial matching of the feature points, it is necessary to then remove mismatching points, which is also referred to as purification of matching pairs, thereby improving the matching accuracy.

In some embodiments, the to-be-annotated image may be matched with the annotated image to obtain an affine transformation matrix in the following manner:

obtaining a template region according to the to-be-annotated image; obtaining a search region according to the annotated image, a size of the search region is greater than a size of the template region; matching the template region with the search region to obtain a feature point matching result; and obtaining the affine transformation matrix through calculation according to the matching result.

In some embodiments, matching between the to-be-annotated image and the annotated image may be performed based on image grayscale. The grayscale image is an image only including brightness information but not including color information, and is generally a black and white image. The brightness of the grayscale image is continuously changed from light to dark, and the brightness of each pixel may be represented by a value ranging from 0 to 255. 0 represents that the pixel is pure black, 255 represents pure white, and other values represent gray.

During actual application, a template region (a size of m×n) is obtained from a to-be-annotated image, and a search region (a size of M×N) is obtained from an annotated image, where the size of the search region is greater than the size of the template region, and the template region is then matched with the search region to obtain a feature point matching result. The affine transformation matrix is obtained through calculation according to the matching result. In this way, image matching is implemented by using a one-dimensional or two-dimensional sliding template in space, thereby achieving a relatively high matching rate. Different matching algorithms are formed according to different selection templates and criteria.

During actual implementation, a region matched with the template region needs to be found from the search region. If the search region with the size of M×N is extracted from the annotated image, and the template region with the size of m×n is extracted from the to-be-annotated image, a similarity between the template region and the search region is calculated. By using a traversal searching method, similarities are calculated between all the search regions and all the template regions that may be obtained, a search region that is most similar to the template region (that is, having a smallest grayscale difference with template pixels) is used as a final matching result, and an affine transformation matrix is obtained through calculation according to the matching result.

In some embodiments, the affine transformation matrix may be obtained by using a matching method based on deep learning (DL). For example, the to-be-annotated image may be matched with the annotated image to obtain an affine transformation matrix in the following manner:

determining a result of matching between the to-be-annotated image and the annotated image by using an image matching network model; and obtaining the affine transformation matrix through calculation according to the to-be-annotated image and the annotated image when the result of matching indicates that the matching succeeds. In this way, the to-be-annotated image and the annotated image are inputted to the image matching network model, to output a result of matching between the to-be-annotated image and the annotated image. If the matching succeeds, it indicates that affine transformation may be performed. That is, the affine transformation matrix is obtained through calculation according to the to-be-annotated image and the annotated image. The method no longer relies on observation and professional knowledge of researchers, but relies on training of data, thereby achieving very high matching accuracy.

During actual implementation, the feature points of the to-be-annotated image and the annotated image may be extracted by using the image matching network model, and the image annotation apparatus matches the feature point of the to-be-annotated image with the feature point of the annotated image, to obtain the affine transformation matrix through calculation, thereby implementing transformation from the annotated image to the to-be-annotated image.

In some embodiments, the affine transformation matrix of the annotated image and the to-be-annotated image may be directly obtained by using the image matching network model, thereby implementing transformation from the annotated image to the to-be-annotated image.

Figure 8:
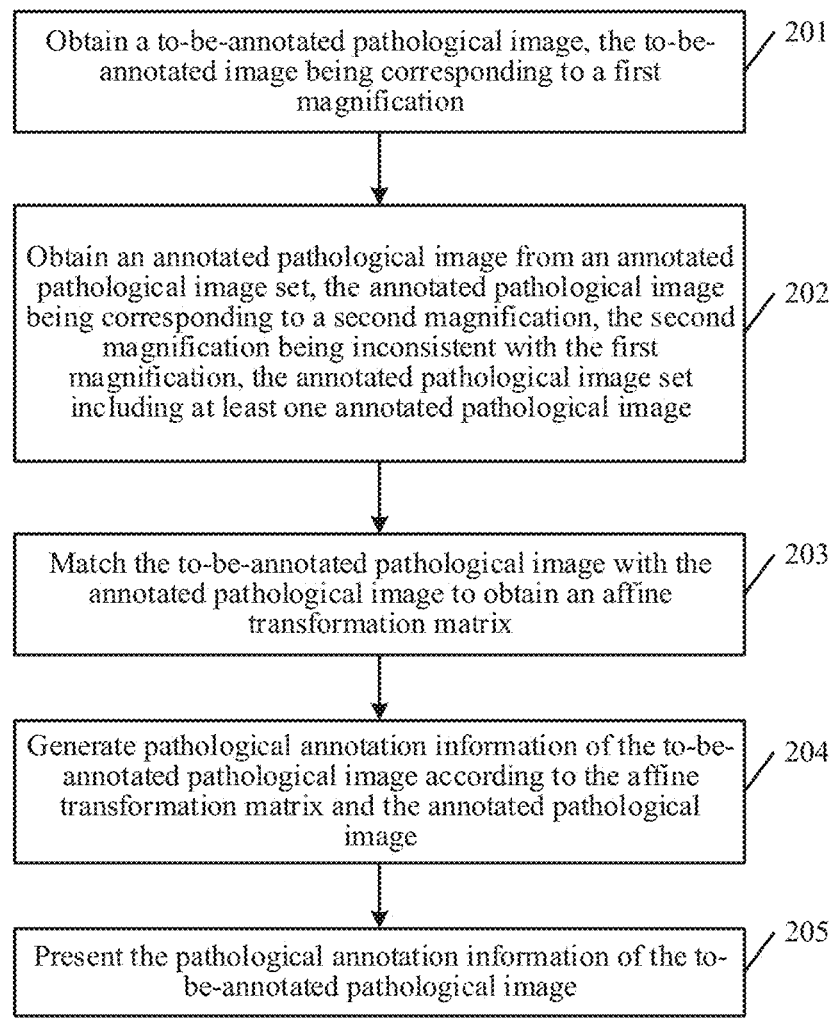
FIG. 8 is a schematic flowchart of an annotation presentation method based on a pathological image according to an embodiment of this application.

With reference to the foregoing description, the annotation presentation method based on a pathological image provided in this application is described below. The method may be implemented by the terminal or the server alone, or may be cooperatively implemented by the terminal and the server. For example, the method is implemented by the terminal device. FIG. 8 is a schematic flowchart of an annotation presentation method based on a pathological image according to an embodiment of this application. Referring to FIG. 8, the annotation presentation method based on a pathological image in this embodiment of this application includes the following steps:

201. The terminal device obtains a to-be-annotated pathological image, the to-be-annotated image corresponding to a first magnification.

During actual implementation, the terminal device obtains the to-be-annotated pathological image, the to-be-annotated pathological image corresponding to the first magnification. The first magnification may be 100 times.

202. Obtain an annotated pathological image from an annotated pathological image set, the annotated pathological image corresponding to a second magnification, the second magnification different from with the first magnification, the annotated pathological image set including at least one annotated pathological image.

In some embodiments, the terminal device obtains the annotated pathological image from the annotated pathological image set. The annotated pathological image set includes the at least one annotated pathological image, the annotated pathological image corresponding to the second magnification. The second magnification is less than the first magnification, or the second magnification is greater than the first magnification. If only low-magnification pathological images are annotated, and high-magnification pathological images are then registered with the low-magnification pathological images to obtain annotations of the high-magnification pathological images, the first magnification is less than the second magnification. If only high-magnification pathological images are annotated, and low-magnification pathological images are then registered with the high-magnification pathological images to obtain annotations of the low-magnification pathological images, the first magnification is greater than the second magnification.

203. Match the to-be-annotated pathological image with the annotated pathological image to obtain an affine transformation matrix.

In some embodiments, the terminal device matches the to-be-annotated pathological image with the annotated pathological image, for example, to obtain an affine transformation matrix through affine transformation. The affine transformation is a linear transformation between two-dimensional coordinates.

After a matching point pair of the to-be-annotated pathological image and the annotated pathological image is obtained, the affine transformation matrix may be calculated, to implement transformation from the original image (the annotated pathological image) to a new image (the to-be-annotated pathological image). After the affine transformation matrix is obtained, the same transformation may be performed on an annotation of the original image (the annotated pathological image), to obtain a migrated annotation on the new image (the to-be-annotated pathological image).

204. Generate pathological annotation information of the to-be-annotated pathological image according to the affine transformation matrix and the annotated pathological image.

In some embodiments, the terminal device determines a position relationship between the to-be-annotated pathological image and the annotated pathological image according to the affine transformation matrix. It is assumed that the annotated pathological image includes an annotation of a region A, and it can be determined according to the affine transformation matrix that the region A also appears in the to-be-annotated pathological image. Therefore, the annotation of the region A is migrated to the to-be-annotated pathological image.

205. Present the pathological annotation information of the to-be-annotated pathological image.

Figure 9:
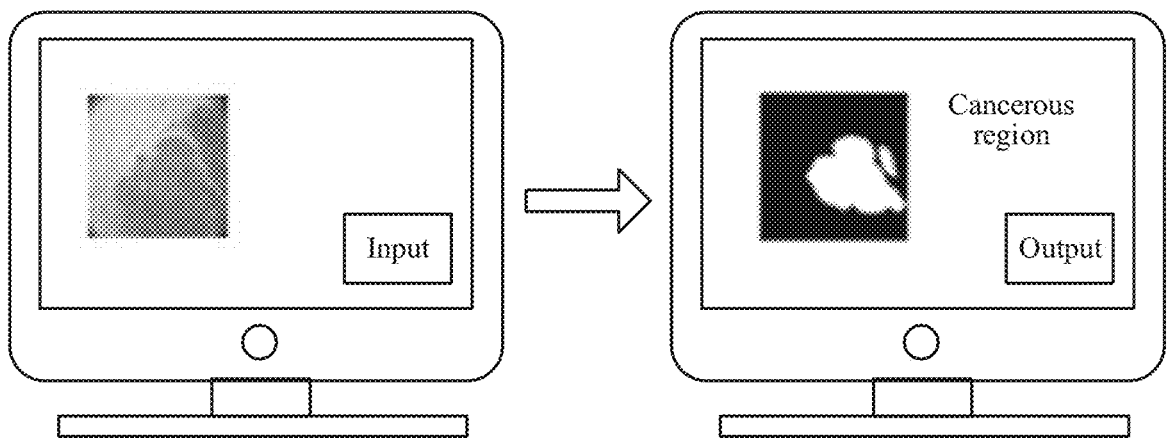
FIG. 9 is a schematic diagram of an interface for presenting pathological annotation information according to an embodiment of this application.

In this embodiment, after generating the pathological annotation information of the to-be-annotated pathological image, the terminal device presents the pathological annotation information of the to-be-annotated pathological image. FIG. 9 is a schematic diagram of an interface for presenting pathological annotation information according to an embodiment of this application. Referring to FIG. 9, a user may input a to-be-annotated pathological image, and the terminal device migrates an annotation to the to-be-annotated pathological image through affine transformation by using pre-annotated other pathological images, so that the terminal device presents, on a display interface, the to-be-annotated pathological image pertaining to a cancerous region.

Through the application of the annotation presentation method based on a pathological image provided in this embodiment of this application, annotations corresponding to pathological images at different magnifications may be migrated. For example, annotations may be migrated from low-magnification pathological images to high-magnification pathological images, thereby reducing the manual annotation amount and avoiding repeated annotations, and further improving annotation efficiency and reducing labor costs. In addition, the terminal device may further present the annotation result to medical staff, so that the medical staff more intuitively determines information reflected by the pathological image.

Figure 10:
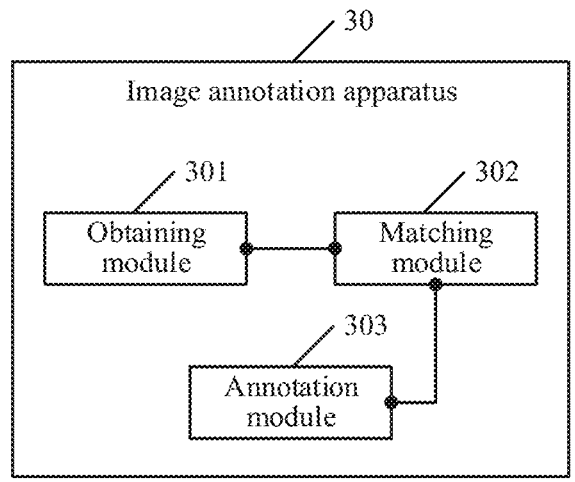
FIG. 10 is a schematic structural diagram of compositions of an image annotation apparatus according to an embodiment of this application.

The image annotation apparatus for implementing the image annotation method in this embodiment of this application is described below in detail. FIG. 10 is a schematic structural diagram of compositions of an image annotation apparatus according to an embodiment of this application. Referring to FIG. 10, the image annotation apparatus 30 includes:

an obtaining module 301, configured to obtain a to-be-annotated image, the to-be-annotated image corresponding to a first magnification, the obtaining module 301 further configured to obtain an annotated image from an annotated image set, the annotated image corresponding to a second magnification, the second magnification different from the first magnification, the annotated image set including at least one annotated image;

a matching module 302, configured to match the to-be-annotated image with the annotated image obtained by the obtaining module 301 to obtain an affine transformation matrix; and an annotation module 303, configured to generate annotation information of the to-be-annotated image according to the affine transformation matrix obtained through matching by the matching module 302 and the annotated image.

Through the application of the image annotation apparatus provided in this embodiment of this application, annotations corresponding to images at different magnifications may be migrated. For example, annotations may be migrated from low-magnification images to high-magnification images, thereby reducing the manual annotation amount and avoiding repeated annotations, and further improving annotation efficiency and reducing labor costs.

In some embodiments, the obtaining module 301 is further configured to obtain a first annotated image and a second annotated image from the annotated image set;

the matching module 302 is further configured to: match the to-be-annotated image with the first annotated image to obtain a first affine transformation matrix; and match the to-be-annotated image with the second annotated image to obtain a second affine transformation matrix; and the annotation module 303 is further configured to: generate first annotation information of the to-be-annotated image according to the first affine transformation matrix and the first annotated image;

generate second annotation information of the to-be-annotated image according to the second affine transformation matrix and the second annotated image; and generate the annotation information of the to-be-annotated image according to the first annotation information and the second annotation information.

In some embodiments, the obtaining module 301 is further configured to obtain a plurality of annotated images from the annotated image set, the plurality of annotated images having overlapping parts;

the matching module 302 is further configured to: splice the plurality of annotated images to obtain a to-be-matched image; and match the to-be-annotated image with the to-be-matched image to obtain the affine transformation matrix; and the annotation module 303 is further configured to generate the annotation information of the to-be-annotated image according to the affine transformation matrix and the to-be-matched image.

In the foregoing manner, another solution of annotating a to-be-annotated image based on a plurality of annotated images is designed, to effectively improve the annotation accuracy and enhance the annotation adaptability, thereby improving the feasibility and flexibility of the solution.

Figure 11:
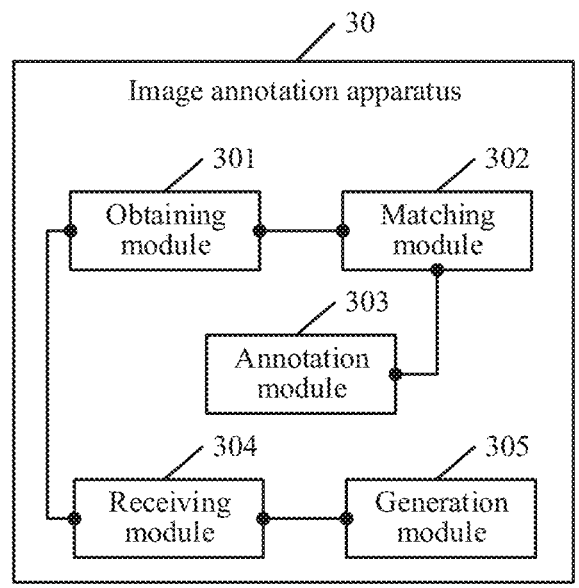
FIG. 11 is a schematic structural diagram of compositions of an image annotation apparatus according to an embodiment of this application.

FIG. 11 is a schematic structural diagram of compositions of an image annotation apparatus 30 according to an embodiment of this application. Referring to FIG. 11, the image annotation apparatus 30 includes the obtaining module 301, the matching module 302, and the annotation module 303, and may further include a receiving module 304 and a generation module 305.

The obtaining module 301 is further configured to obtain a target annotation region before obtaining the annotated image from the annotated image set.

The obtaining module 301 is further configured to obtain a plurality of to-be-processed images according to the target annotation region, the plurality of to-be-processed images including the to-be-annotated image and M annotatable images, M is an integer greater than or equal to 1.

The receiving module 304 is configured to receive annotation information corresponding to each annotatable image in the M annotatable images.

The generation module 305 is configured to generate the annotated image set according to the annotation information corresponding to the each annotatable image received by the receiving module 304, the annotated image set including M annotated images.

In the foregoing manner, during manual annotation, only some images rather than all images in the to-be-processed images need to be annotated, thereby reducing annotation costs and improving annotation efficiency.

In some embodiments, the receiving module 304 is further configured to: receive an image annotation instruction, the image annotation instruction carrying an identifier of an annotatable image; and
  annotate the annotatable image according to the image annotation instruction to obtain annotation information corresponding to the annotatable image.

In some embodiments, the matching module 302 is further configured to: obtain a first feature point set of the to-be-annotated image, the first feature point set including a plurality of feature points;
  obtain a second feature point set of the annotated image, the second feature point set including a plurality of feature points;
  match the first feature point set with the second feature point set to obtain a matching result; and
  obtain the affine transformation matrix through calculation according to the matching result.

In the foregoing manner, a similarity between the two images is determined by using a method of matching the feature points, and the affine transformation matrix is generated based on a matching relationship between the feature points. Considering that an image includes many feature points, a richer amount of information is obtained, so that higher matching accuracy is achieved.

In some embodiments, the matching module 302 is further configured to: determine a to-be-matched feature point from the second feature point set;
  determine a first feature point and a second feature point from the first feature point set according to the to-be-matched feature point;
  determine a first distance according to the first feature point and the to-be-matched feature point, and determine a second distance according to the second feature point and the to-be-matched feature point, the first distance is less than the second distance; and
  determine, when a ratio of the first distance to the second distance is less than a ratio threshold, that the first feature point is successfully matched with the to-be-matched feature point.

In the foregoing manner, during matching of the feature points, a nearest neighbor of a query point may be found based on a similarity measurement criterion and a search policy, but two points having the shortest distance are not necessarily a correct matching point pair. To reduce errors during subsequent processing, based on initial matching of the feature points, it is necessary to then remove mismatching points, which is also referred to as purification of matching pairs, thereby improving the matching accuracy.

In some embodiments, the matching module 302 is further configured to: obtain a template region according to the to-be-annotated image;
  obtain a search region according to the annotated image, a size of the search region is greater than a size of the template region;
  match the template region with the search region to obtain a feature point matching result; and
  obtain the affine transformation matrix through calculation according to the matching result.

In the foregoing manner, image matching is implemented by using a one-dimensional or two-dimensional sliding template in space, thereby achieving a relatively high matching rate. Different matching algorithms are formed according to different selection templates and criteria.

In some embodiments, the matching module 302 is further configured to: determine a result of matching between the to-be-annotated image and the annotated image by using an image matching network model; and
  obtain the affine transformation matrix through calculation according to the to-be-annotated image and the annotated image when the result of matching indicates that the matching succeeds.

In the foregoing manner, the image matching method based on deep learning no longer relies on observation and professional knowledge of researchers, but relies on data training, thereby achieving high matching accuracy.

Figure 12:
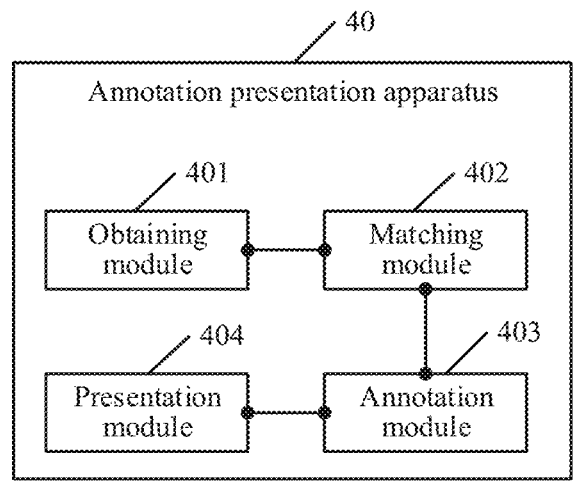
FIG. 12 is a schematic structural diagram of compositions of an annotation presentation apparatus according to an embodiment of this application.

The annotation presentation apparatus provided in this embodiment of this application is described below in detail. FIG. 12 is a schematic structural diagram of compositions of an annotation presentation apparatus according to an embodiment of this application. Referring to FIG. 12, the annotation presentation apparatus 40 includes:
  an obtaining module 401, configured to obtain a to-be-annotated pathological image, the to-be-annotated image corresponding to a first magnification,
  the obtaining module 401 further configured to obtain an annotated pathological image from an annotated pathological image set, the annotated pathological image corresponding to a second magnification, the second magnification is distinct from the first magnification, the annotated pathological image set including at least one annotated pathological image;
  a matching module 402, configured to match the to-be-annotated pathological image with the annotated pathological image obtained by the obtaining module 401 to obtain an affine transformation matrix;
  an annotation module 403, configured to generate pathological annotation information of the to-be-annotated pathological image according to the affine transformation matrix obtained through matching by the matching module 402 and the annotated pathological image; and
  a presentation module 404, configured to present the pathological annotation information of the to-be-annotated pathological image obtained through annotation by the annotation module 403.

In the foregoing manner, annotations corresponding to pathological images at different magnifications may be migrated. For example, the annotations may be migrated from the low-magnification pathological images to the high-magnification pathological images, thereby reducing the manual annotation amount and avoiding repeated annotations, and further improving annotation efficiency and reducing labor costs. In addition, the terminal device may further present the annotation result to medical staff, so that the medical staff more intuitively determines information reflected by the pathological image.

Figure 13:
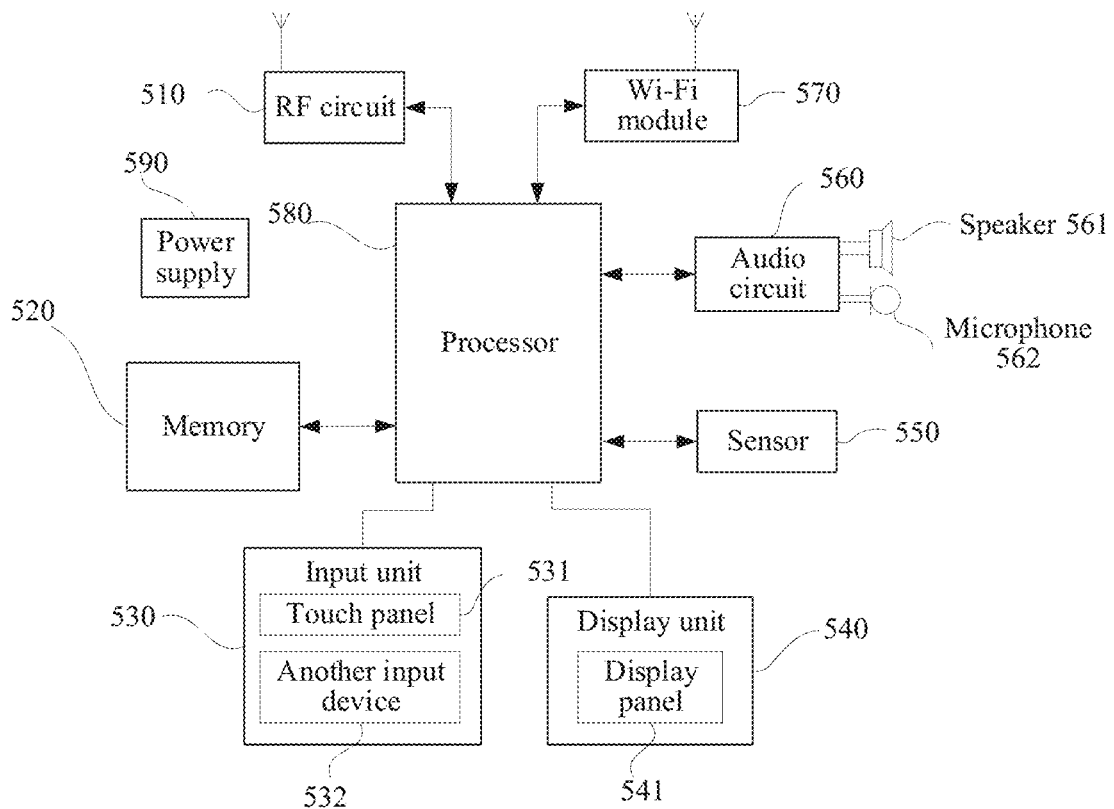
FIG. 13 is a schematic structural diagram of a terminal device according to an embodiment of this application.

In some embodiments, the image annotation apparatus and the annotation presentation apparatus provided in the embodiments of this application may be located in a terminal device. FIG. 13 is a schematic structural diagram of a terminal device according to an embodiment of this application. As shown in FIG. 13, for ease of description, only parts related to the embodiments of this application are shown. For specific technical details that are not disclosed, refer to the method part in the embodiments of this application. The terminal device may be any terminal device including a mobile phone, a tablet computer, a personal digital assistant (PDA), a point of sales (POS), and an on-board computer, and the terminal device being a mobile phone is used as an example.

FIG. 13 is a block diagram of a partial structure of a terminal device according to an embodiment of this application. Referring to FIG. 13, the terminal device includes components such as a radio frequency (RF) circuit 510, a memory 520, an input unit 530, a display unit 540, a sensor 550, an audio circuit 560, a wireless fidelity (Wi-Fi) module 570, a processor 580, and a power supply 590. A person skilled in the art may understand that the terminal structure shown in FIG. 13 does not constitute a limitation on the terminal, and may include more or fewer components than shown in the figure, or some components may be combined, or a different component deployment may be used.

The RF circuit 510 may be configured to receive and transmit signals in an information receiving and transmitting process or a call process. Specifically, the RF circuit receives downlink information from a base station, then delivers the downlink information to the processor 580 for processing, and transmits designed uplink data to the base station. Generally, the RF circuit 510 includes, but not limited to, an antenna, at least one amplifier, a transceiver, a coupler, a low noise amplifier (LNA), and a duplexer. In addition, the RF circuit 510 may also communicate with a network and another device by means of wireless communication. The wireless communication may use any communication standard or protocol, including, but not limited to, Global system for mobile communications (GSM), general packet radio service (GPRS), Code Division Multiple Access (CDMA), Wideband Code Division Multiple Access (WCDMA), Long Term Evolution (LTE), email, Short Messaging Service (SMS), and the like.

The memory 520 may be configured to store a software program and module. The processor 580 runs the software program and module stored in the memory 520, to implement various functional applications and data processing of the mobile phone. The memory 520 may mainly include a program storage area and a data storage area. The program storage area may store an operating system, an application program required by at least one function (such as a sound playback function and an image display function), and the like. The data storage area may store data (such as audio data and an address book) created according to the use of the mobile phone, and the like. In addition, the memory 520 may include a high-speed random access memory, and may also include a non-volatile memory, for example, at least one magnetic disk storage device, a flash memory, or another volatile solid-state storage device.

The input unit 530 may be configured to receive input digit or character information, and generate a keyboard signal input related to the user setting and function control of the mobile phone. In actual application, the input unit 530 may include a touch panel 531 and another input device 532.

The touch panel 531, which may also be referred to as a touchscreen, may collect a touch operation of a user on or near the touch panel (such as an operation of a user on or near the touch panel 531 by using any suitable object or accessory such as a finger or a stylus), and drive a corresponding connection apparatus according to a preset program. In some embodiments, the touch panel 531 may include two parts: a touch detection apparatus and a touch controller. The touch detection apparatus detects a touch orientation of the user, detects a signal generated by the touch operation, and transfers the signal to the touch controller. The touch controller receives the touch information from the touch detection apparatus, converts the touch information into touch point coordinates, and transmits the touch point coordinates to the processor 580. Moreover, the touch controller may receive and execute a command transmitted from the processor 580. In addition, the touch panel 531 may be a resistive, capacitive, infrared, or surface acoustic touch panel. Besides the touch panel 531, the input unit 530 may further include another input device 532. In actual application, the another input device 532 may include, but not limited to, one or more of a physical keyboard, a functional key (such as a volume control key or a switch key), a track ball, a mouse, and a joystick.

The display unit 540 may be configured to display information inputted by the user or information provided for the user, and various menus of the mobile phone. The display unit 540 may include a display panel 541. In some embodiments, the display panel 541 may be configured in the form of a liquid crystal display (LCD), an organic light-emitting diode (OLED), or the like. The touch panel 531 may cover the display panel 541. After detecting a touch operation on or near the touch panel, the touch panel 531 transfers the touch operation to the processor 580, to determine a type of a touch event. Then, the processor 580 provides a corresponding visual output on the display panel 541 according to the type of the touch event. Although in FIG. 13, the touch panel 531 and the display panel 541 are used as two separate parts to implement input and output functions of the mobile phone, in some embodiments, the touch panel 531 and the display panel 541 may be integrated to implement the input and output functions of the mobile phone.

The terminal device may further include at least one sensor 550 such as an optical sensor, a motion sensor, and another sensor. In actual application, the optical sensor may include an ambient light sensor and a proximity sensor. The ambient light sensor may adjust luminance of the display panel 541 according to brightness of the ambient light. The proximity sensor may switch off the display panel 541 and/or backlight when the mobile phone is moved to the ear. As one type of motion sensor, an acceleration sensor can detect magnitude of accelerations in various directions (generally on three axes), may detect magnitude and a direction of the gravity when static, and may be applied to an application that recognizes the attitude of the mobile phone (for example, switching between landscape orientation and portrait orientation, a related game, and magnetometer attitude calibration), a function related to vibration recognition (such as a pedometer and a knock), and the like. Other sensors, such as a gyroscope, a barometer, a hygrometer, a thermometer, and an infrared sensor, which may be configured in the mobile phone, are not further described herein.

The audio circuit 560, a speaker 561, and a microphone 562 may provide audio interfaces between the user and the mobile phone. The audio circuit 560 may transmit, to the speaker 561, an electric signal converted from received audio data. The speaker 561 converts the electric signal into a sound signal for output. On the other hand, the microphone 562 converts a collected sound signal into an electric signal. The audio circuit 560 receives the electric signal and converts the electric signal into audio data, and outputs the audio data to the processor 580 for processing. Then, the processor sends the audio data to, for example, another terminal by using the RF circuit 510, or outputs the audio data to the memory 520 for further processing.

Wi-Fi is a short distance wireless transmission technology. The mobile phone may help, by using the Wi-Fi module 570, a user to receive and transmit an email, browse a web page, access stream media, and the like. This provides wireless broadband Internet access for the user. Although FIG. 13 shows the Wi-Fi module 570, it may be understood that the Wi-Fi module is not a necessary component of the mobile phone, and the Wi-Fi module may be omitted as required provided that the scope of the essence of the present invention is not changed.

The processor 580 is the control center of the mobile phone, and is connected to various parts of the mobile phone by using various interfaces and lines. By running or executing the software program and/or module stored in the memory 520, and invoking data stored in the memory 520, the processor performs various functions and data processing of the mobile phone, thereby performing overall monitoring on the mobile phone. The processor 580 may include one or more processing units. In some embodiments, the processor 580 may integrate an application processor and a modem. The application processor mainly processes an operating system, a user interface, an application program, and the like. The modem mainly processes wireless communication. It may be understood that the foregoing modem may either not be integrated into the processor 580.

The terminal further includes the power supply 590 (such as a battery) for supplying power to the components. In some embodiments, the power supply may be logically connected to the processor 580 by using a power management system, thereby implementing functions such as charging, discharging, and power consumption management by using the power management system.

Although not shown, the terminal may further include a camera, a Bluetooth module, and the like, and details are not described herein again.

In this embodiment of this application, the processor 580 included in the terminal device further has the following functions:

obtaining a to-be-annotated image, the to-be-annotated image corresponding to a first magnification;

obtaining an annotated image from an annotated image set, the annotated image being corresponding to a second magnification, the second magnification different from the first magnification, the annotated image set including at least one annotated image;

matching the to-be-annotated image with the annotated image to obtain an affine transformation matrix; and generating annotation information of the to-be-annotated image according to the affine transformation matrix and the annotated image.

In some embodiments, the processor 580 is further configured to perform the following steps:

obtaining a first annotated image and a second annotated image from the annotated image set;

matching the to-be-annotated image with the first annotated image to obtain a first affine transformation matrix;

matching the to-be-annotated image with the second annotated image to obtain a second affine transformation matrix;

generating first annotation information of the to-be-annotated image according to the first affine transformation matrix and the first annotated image;

generating second annotation information of the to-be-annotated image according to the second affine transformation matrix and the second annotated image; and generating the annotation information of the to-be-annotated image according to the first annotation information and the second annotation information.

In some embodiments, the processor 580 is further configured to perform the following steps:

obtaining a plurality of annotated images from the annotated image set, the plurality of annotated images having overlapping parts;

splicing the plurality of annotated images to obtain a to-be-matched image; and matching the to-be-annotated image with the to-be-matched image to obtain the affine transformation matrix; and generating the annotation information of the to-be-annotated image according to the affine transformation matrix and the to-be-matched image.

In some embodiments, the processor 580 is further configured to perform the following steps:

obtaining a target annotation region;

obtaining a plurality of to-be-processed images according to the target annotation region, the plurality of to-be-processed images including the to-be-annotated image and M annotatable images, M is an integer greater than or equal to 1;

receiving annotation information corresponding to each annotatable image in the M annotatable images; and generating the annotated image set according to the annotation information corresponding to the each annotatable image, the annotated image set including M annotated images.

In some embodiments, the processor 580 is further configured to perform the following steps:

receiving an image annotation instruction, the image annotation instruction carrying an identifier of an annotatable image; and annotating the annotatable image according to the image annotation instruction to obtain annotation information corresponding to the annotatable image.

In some embodiments, the processor 580 is further configured to perform the following steps:

obtaining a first feature point set of the to-be-annotated image, the first feature point set including a plurality of feature points;

obtaining a second feature point set of the annotated image, the second feature point set including a plurality of feature points;

matching the first feature point set with the second feature point set to obtain a matching result; and obtaining the affine transformation matrix through calculation according to the matching result.

In some embodiments, the processor 580 is further configured to perform the following steps:

determining a to-be-matched feature point from the second feature point set;

determining a first feature point and a second feature point from the first feature point set according to the to-be-matched feature point;

determining a first distance according to the first feature point and the to-be-matched feature point, and determining a second distance according to the second feature point and the to-be-matched feature point, the first distance is less than the second distance; and determining, when a ratio of the first distance to the second distance is less than a ratio threshold, that the first feature point is successfully matched with the to-be-matched feature point.

In some embodiments, the processor 580 is further configured to perform the following steps:

obtaining a template region according to the to-be-annotated image;

obtaining a search region according to the annotated image, a size of the search region is greater than a size of the template region;

matching the template region with the search region to obtain a feature point matching result; and obtaining the affine transformation matrix through calculation according to the matching result.

In some embodiments, the processor 580 is further configured to perform the following steps:

determining a result of matching between the to-be-annotated image and the annotated image by using an image matching network model; and obtaining the affine transformation matrix through calculation according to the to-be-annotated image and the annotated image when the result of matching indicates that the matching succeeds.

In this embodiment of this application, the processor 580 included in the terminal device further has the following functions:

obtaining a to-be-annotated pathological image, the to-be-annotated image corresponding to a first magnification;

obtaining an annotated pathological image from an annotated pathological image set, the annotated pathological image corresponding to a second magnification, the second magnification different from the first magnification, the annotated pathological image set including at least one annotated pathological image;

matching the to-be-annotated pathological image with the annotated pathological image to obtain an affine transformation matrix;

generating pathological annotation information of the to-be-annotated pathological image according to the affine transformation matrix and the annotated pathological image; and presenting the pathological annotation information of the to-be-annotated pathological image.

Figure 14:
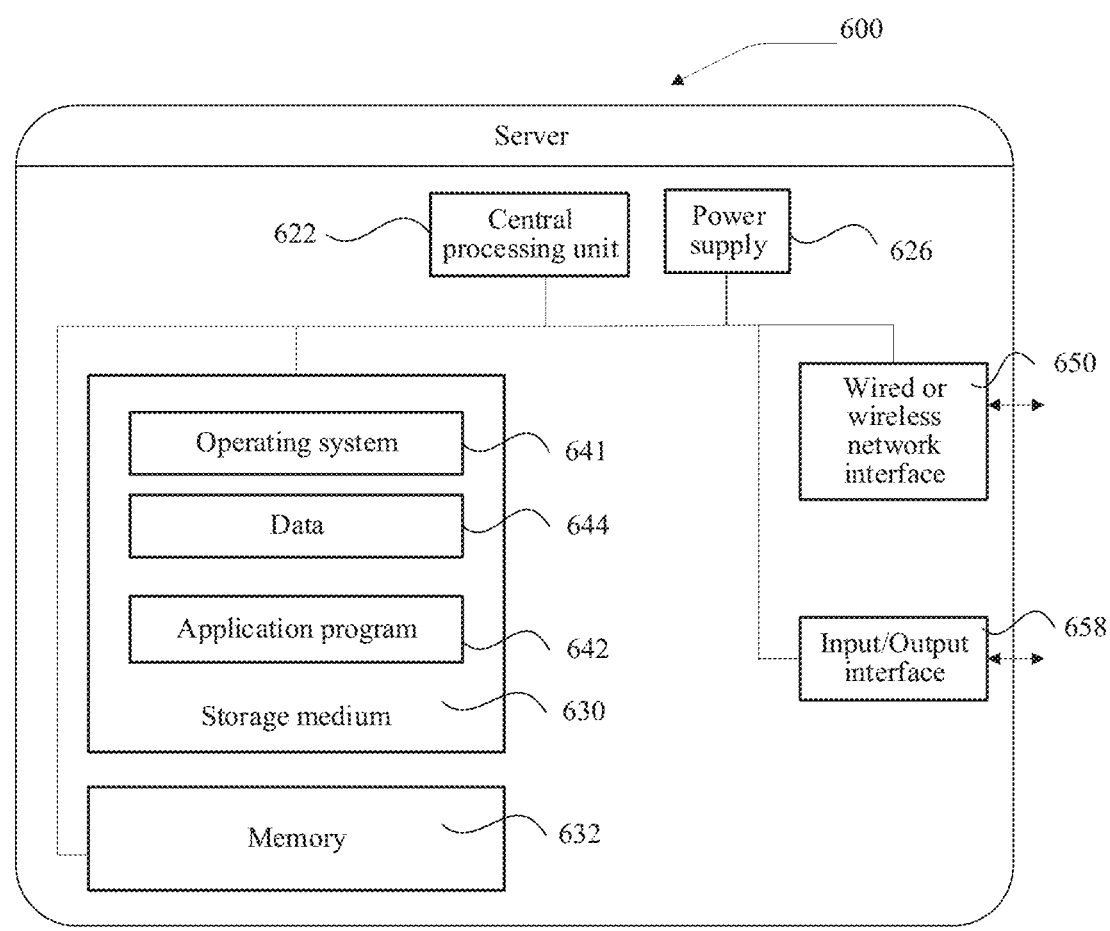
FIG. 14 is a schematic structural diagram of a server according to an embodiment of this application.

FIG. 14 is a schematic structural diagram of a server according to an embodiment of this application. Referring to FIG. 14, the server 600 may vary greatly due to different configurations or performance, and may include one or more central processing units (CPUs) 622 (for example, one or more processors) and a memory 632, and one or more non-transitory computer readable storage media 630 (for example, one or more mass storage devices) that store application programs 642 or data 644. The memory 632 and the storage media 630 may implement transient storage or permanent storage. The program stored in the storage media 630 may include one or more modules (not shown), and each module may include a series of instruction operations for the server. Furthermore, the CPU 622 may be configured to communicate with the storage media 630, and perform, on the server 600, the series of instruction operations in the storage media 630.

The server 600 may further include one or more power supplies 626, one or more wired or wireless network interfaces 650, one or more input/output interfaces 658, and/or one or more operating systems 641 such as Windows Server™, Mac OS X™, Unix™, Linux™, and FreeBSD™.

The steps performed by the server in the foregoing embodiments may be based on the server structure shown in FIG. 14.

In this embodiment of this application, the CPU 622 included in the server further has the following functions:

obtaining a to-be-annotated image, the to-be-annotated image corresponding to a first magnification;

obtaining an annotated image from an annotated image set, the annotated image corresponding to a second magnification, the second magnification different from the first magnification, the annotated image set including at least one annotated image;

matching the to-be-annotated image with the annotated image to obtain an affine transformation matrix; and generating annotation information of the to-be-annotated image according to the affine transformation matrix and the annotated image.

A person skilled in the art can clearly understand that for convenience and conciseness of description, for specific working processes of the foregoing described system, apparatus and unit, refer to the corresponding processes in the foregoing method embodiments, and details are not described herein again.

In the several embodiments provided in this application, the disclosed system, apparatus, and method may be implemented in other manners. For example, the described apparatus embodiment is merely exemplary. For example, the unit division is merely a logical function division and may be other division during actual implementation. For example, a plurality of units or components may be combined or integrated into another system, or some features may be ignored or not performed. In addition, the displayed or discussed mutual couplings or direct couplings or communication connections may be implemented by using some interfaces. The indirect couplings or communication connections between the apparatuses or units may be implemented in electronic, mechanical, or other forms.

The units described as separate components may or may not be physically separated, and the components displayed as units may or may not be physical units, and may be located in one place or may be distributed over a plurality of network units. Some or all of the units may be selected according to actual requirements to achieve the objectives of the solutions of the embodiments.

In addition, functional units in the embodiments of this application may be integrated into one processing unit, or each of the units may exist alone physically, or two or more units may be integrated into one unit. The integrated unit may be implemented in a form of hardware, or may be implemented in a form of a software functional unit.

When the integrated unit is implemented in the form of a software functional unit and sold or used as an independent product, the integrated unit may be stored in a computer-readable storage medium. Based on such an understanding, the technical solutions of this application essentially, or the part contributing to the related technology, or all or some of the technical solutions may be implemented in the form of a software product. The computer software product is stored in a storage medium and includes several instructions for instructing a computer device (which may be a personal computer, a server, a network device, or the like) to perform all or some of the steps of the methods described in the embodiments of this application. The foregoing storage medium includes: any medium that can store program code, such as a USB flash drive, a removable hard disk, a read-only memory (ROM), a random access memory (RAM), a magnetic disk, or an optical disc.

The foregoing embodiments are merely intended for describing the technical solutions of this application, but not for limiting this application. Although this application is described in detail with reference to the foregoing embodiments, persons of ordinary skill in the art understand that they may still make modifications to the technical solutions described in the foregoing embodiments or make equivalent replacements to some technical features thereof, without departing from the spirit and scope of the technical solutions of the embodiments of this application.

Note that the various embodiments described above can be combined with any other embodiments described herein. The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

As used herein, the term "unit" or "module" refers to a computer program or part of the computer program that has a predefined function and works together with other related parts to achieve a predefined goal and may be all or partially implemented by using software, hardware (e.g., processing circuitry and/or memory configured to perform the predefined functions), or a combination thereof. Each unit or module can be implemented using one or more processors (or processors and memory). Likewise, a processor (or processors and memory) can be used to implement one or more modules or units. Moreover, each module or unit can be part of an overall module that includes the functionalities of the module or unit. The division of the foregoing functional modules is merely used as an example for description when the systems, devices, and apparatus provided in the foregoing embodiments performs matching and/or annotating. In practical application, the foregoing functions may be allocated to and completed by different functional modules according to requirements, that is, an inner structure of a device is divided into different functional modules to implement all or a part of the functions described above.

What is claimed is:

1. An image annotation method, comprising:
obtaining a to-be-annotated image having a first magnification;
obtaining a plurality of annotated images from an annotated image set, the plurality of annotated images having overlapping parts and a second magnification that is distinct from the first magnification and annotation information characterizing content of the plurality of annotated images;
matching the to-be-annotated image with the plurality of annotated images to obtain an affine transformation matrix based on the first magnification and the second magnification, further including:
splicing the plurality of annotated images to obtain a to-be-matched annotated image; and
matching the to-be-annotated image with the to-be-matched annotated image to obtain the affine transformation matrix; and
generating annotation information characterizing content of the to-be-annotated image by migrating the annotation information characterizing content of the plurality of annotated images according to the affine transformation matrix associated with the to-be-matched annotated image.

2. The method according to claim 1, further comprising: prior to obtaining the annotated image:
obtaining a target annotation region;
obtaining a plurality of to-be-processed images according to the target annotation region, the plurality of to-be-processed images comprising the to-be-annotated image and M annotatable images, wherein M is an integer greater than or equal to 1;
receiving annotation information corresponding to each annotatable image in the M annotatable images; and
generating the annotated image set according to the annotation information corresponding to the each annotatable image, the annotated image set comprising M annotated images.

3. The method according to claim 2, wherein receiving the annotation information further comprises:
receiving an image annotation instruction, the image annotation instruction carrying an identifier of an annotatable image; and
annotating the annotatable image according to the image annotation instruction to obtain annotation information corresponding to the annotatable image.

4. The method according to claim 1, wherein matching the to-be-annotated image with the plurality of annotated images further comprises:
obtaining a first feature point set of the to-be-annotated image, the first feature point set comprising a plurality of feature points;
obtaining a second feature point set of the to-be-matched annotated image, the second feature point set comprising a plurality of feature points;
matching the first feature point set with the second feature point set to obtain a matching result; and
obtaining the affine transformation matrix through calculation according to the matching result.

5. The method according to claim 4, wherein matching the first feature point set with the second feature point set to obtain a matching result further comprises:
determining a to-be-matched feature point from the second feature point set;
determining a first feature point and a second feature point from the first feature point set according to the to-be-matched feature point;
determining a first distance according to the first feature point and the to-be-matched feature point, and determining a second distance according to the second feature point and the to-be-matched feature point, the first distance being less than the second distance; and
determining, when a ratio of the first distance to the second distance is less than a ratio threshold, that the first feature point is successfully matched with the to-be-matched feature point.

6. The method according to claim 1, wherein matching the to-be-annotated image with the plurality of annotated images further comprises:
obtaining a template region according to the to-be-annotated image;
obtaining a search region according to the to-be-matched annotated image, a size of the search region being greater than a size of the template region;

matching the template region with the search region to obtain a feature point matching result; and obtaining the affine transformation matrix through calculation according to the matching result.

7. The method according to claim 1, wherein matching the to-be-annotated image with the plurality of annotated images further comprises:

determining a result of matching between the to-be-annotated image and the to-be-matched annotated image by using an image matching network model; and obtaining the affine transformation matrix through calculation according to the to-be-annotated image and the to-be-matched annotated image when the result of matching indicates that the matching succeeds.

8. A computer device, comprising:

one or more processors; and memory storing one or more programs, that, when executed by the one or more processors, cause the one or more processors to perform operations comprising:

obtaining a to-be-annotated image having a first magnification;

obtaining a plurality of annotated images from an annotated image set, the plurality of annotated images having overlapping parts and a second magnification that is distinct from the first magnification and annotation information characterizing content of the plurality of annotated images;

matching the to-be-annotated image with the plurality of annotated images to obtain an affine transformation matrix based on the first magnification and the second magnification, further including:

splicing the plurality of annotated images to obtain a to-be-matched annotated image; and matching the to-be-annotated image with the to-be-matched annotated image to obtain the affine transformation matrix; and generating annotation information characterizing content of the to-be-annotated image by migrating the annotation information characterizing content of the plurality of annotated images according to the affine transformation matrix associated with the to-be-matched annotated image.

9. The computer device according to claim 8, the operations further comprising:

prior to obtaining the annotated image:

obtaining a target annotation region;

obtaining a plurality of to-be-processed images according to the target annotation region, the plurality of to-be-processed images comprising the to-be-annotated image and M annotatable images, wherein M is an integer greater than or equal to 1;

receiving annotation information corresponding to each annotatable image in the M annotatable images; and generating the annotated image set according to the annotation information corresponding to the each annotatable image, the annotated image set comprising M annotated images.

10. The computer device according to claim 9, wherein receiving the annotation information further comprises:

receiving an image annotation instruction, the image annotation instruction carrying an identifier of an annotatable image; and annotating the annotatable image according to the image annotation instruction to obtain annotation information corresponding to the annotatable image.

11. The computer device according to claim 8, wherein matching the to-be-annotated image with the plurality of annotated images further comprises:

obtaining a first feature point set of the to-be-annotated image, the first feature point set comprising a plurality of feature points;

obtaining a second feature point set of the to-be-matched annotated image, the second feature point set comprising a plurality of feature points;

matching the first feature point set with the second feature point set to obtain a matching result; and obtaining the affine transformation matrix through calculation according to the matching result.

12. The computer device according to claim 11, wherein matching the first feature point set with the second feature point set to obtain a matching result further comprises:

determining a to-be-matched feature point from the second feature point set;

determining a first feature point and a second feature point from the first feature point set according to the to-be-matched feature point;

determining a first distance according to the first feature point and the to-be-matched feature point, and determining a second distance according to the second feature point and the to-be-matched feature point, the first distance being less than the second distance; and determining, when a ratio of the first distance to the second distance is less than a ratio threshold, that the first feature point is successfully matched with the to-be-matched feature point.

13. The computer device according to claim 8, wherein matching the to-be-annotated image with the plurality of annotated images further comprises:

obtaining a template region according to the to-be-annotated image;

obtaining a search region according to the to-be-matched annotated image, a size of the search region being greater than a size of the template region;

matching the template region with the search region to obtain a feature point matching result; and obtaining the affine transformation matrix through calculation according to the matching result.

14. The computer device according to claim 8, wherein matching the to-be-annotated image with the plurality of annotated images further comprises:

determining a result of matching between the to-be-annotated image and the to-be-matched annotated image by using an image matching network model; and obtaining the affine transformation matrix through calculation according to the to-be-annotated image and the to-be-matched annotated image when the result of matching indicates that the matching succeeds.

15. A non-transitory computer readable storage medium storing instructions that, when executed by one or more processors of a computer device, cause the one or more processors to perform operations comprising:

obtaining a to-be-annotated image having a first magnification;

obtaining a plurality of annotated images from an annotated image set, the plurality of annotated images having overlapping parts and a second magnification that is distinct from the first magnification and annotation information characterizing content of the plurality of annotated images;

matching the to-be-annotated image with the plurality of annotated images to obtain an affine transformation matrix based on the first magnification and the second magnification, further including:
  splicing the plurality of annotated images to obtain a to-be-matched annotated image; and
  matching the to-be-annotated image with the to-be-matched annotated image to obtain the affine transformation matrix; and
generating annotation information characterizing content of the to-be-annotated image by migrating the annotation information characterizing content of the plurality of annotated images according to the affine transformation matrix associated with the to-be-matched annotated image.

16. The non-transitory computer readable storage medium according to claim 15, the operations further comprising:
  prior to obtaining the annotated image:
    obtaining a target annotation region;
    obtaining a plurality of to-be-processed images according to the target annotation region, the plurality of to-be-processed images comprising the to-be-annotated image and M annotatable images, wherein M is an integer greater than or equal to 1;
    receiving annotation information corresponding to each annotatable image in the M annotatable images; and
    generating the annotated image set according to the annotation information corresponding to the each annotatable image, the annotated image set comprising M annotated images.

17. The non-transitory computer readable storage medium according to claim 15, wherein matching the to-be-annotated image with the plurality of annotated images further comprises:
  obtaining a first feature point set of the to-be-annotated image, the first feature point set comprising a plurality of feature points;
  obtaining a second feature point set of the to-be-matched annotated image, the second feature point set comprising a plurality of feature points;
  matching the first feature point set with the second feature point set to obtain a matching result; and
  obtaining the affine transformation matrix through calculation according to the matching result.

18. The non-transitory computer readable storage medium according to claim 15, wherein matching the to-be-annotated image with the plurality of annotated images further comprises:
  obtaining a template region according to the to-be-annotated image;
  obtaining a search region according to the to-be-matched annotated image, a size of the search region being greater than a size of the template region;
  matching the template region with the search region to obtain a feature point matching result; and
  obtaining the affine transformation matrix through calculation according to the matching result.

19. The non-transitory computer readable storage medium according to claim 15, wherein matching the to-be-annotated image with the plurality of annotated images further comprises:
  determining a result of matching between the to-be-annotated image and the to-be-matched annotated image by using an image matching network model; and
  obtaining the affine transformation matrix through calculation according to the to-be-annotated image and the to-be-matched annotated image when the result of matching indicates that the matching succeeds.

* * * * *